United States Patent [19]

Thomas et al.

[11] Patent Number: 5,736,669

[45] Date of Patent: Apr. 7, 1998

[54] SYSTEMS FOR BIOREMEDIATING EXPLOSIVES

[75] Inventors: Ronald D. Thomas, Woodland Hills; Lyman G. Bahr, Payson, both of Utah; Walter B. Dunning, Sonora, Calif.; Dean F. Richards, Pleasant Grove, Utah

[73] Assignee: The Ensign-Bickford Company, Simsbury, Conn.

[21] Appl. No.: 658,142

[22] Filed: Jun. 4, 1996

Related U.S. Application Data

[63] Continuation-in-part of Ser. No. 560,074, Nov. 17, 1995, abandoned.

[51] Int. Cl.[6] ............................................. F42C 3/02
[52] U.S. Cl. ........................ 102/293; 588/203; 435/262.5
[58] Field of Search .............................. 102/293, 473; 588/202, 203; 86/49, 50; 89/1.11; 435/262.5

[56] References Cited

U.S. PATENT DOCUMENTS

| | | | |
|---|---|---|---|
| 2,330,110 | 9/1943 | Buchan | 166/21 |
| 3,157,119 | 11/1964 | Porter | 102/21.8 |
| 3,710,718 | 1/1973 | Grant | 102/23 |
| 4,016,117 | 4/1977 | Griffin | 260/17.4 |
| 4,064,941 | 12/1977 | Smith | 166/300 |
| 4,108,728 | 8/1978 | Spinner et al. | 195/127 |

(List continued on next page.)

OTHER PUBLICATIONS

Kaplan, David A., "Biotechnology and Bioremediation for Organic Energetic Compounds," *Organic Energetic Compounds* 373–416 (Paul L. Marinkas ed., 1996).

R. Boopathy et al., *Biological Transformation of 2,4, 6–Trinitrotoluene (TNT) By Soil Bacteria Isolated From TNT–Contaminated Soil*, 47 Bioresource Technology 19 (1994).

R. Boopathy et al., *Biotransformation of 2,4,6–Trinitrotoluene (TNT) By Co–Metabolism With Various Co–Substrates: A Laboratory–Scale Study*, 47 Bioresource Technology 205 (1994).

John P. Knezovich et al., *Chemical and Biological Systems for Treating Waste Streams Contaminated with High Explosives*, paper submitted for JANNAF Safety and Environmental Protection Subcommitte Meeting in Tampa, Florida (Dec. 5–8, 1995).

John P. Knezovich et al., *Chemical and Biological Systems for Regenerating Activated Carbon Contaminated with High Explosives*, paper submitted to Proceedings Demin'94 in Luxembourg, Luxembourg (Nov. 14–16, 1994).

*Primary Examiner*—Charles T. Jordan
*Assistant Examiner*—John R. Hardee
*Attorney, Agent, or Firm*—Trask, Britt & Rossa

[57] ABSTRACT

Technology for in situ remediation of undetonated explosive material. A bioremediating apparatus in the form of a storage chamber houses in moist condition type of microorganisms capable of metabolizing the explosive material. Examples of such microorganisms include Pseudomonas spp., *Escherichia coli, Morganella morganii*, Rhodococcus spp., Comamonas spp., and denitrifying bacteria. The bioremediating apparatus is joined with an explosive apparatus that houses a charge of explosive material. A solution released into the storage chamber by opening a first valve hydrates the microorganisms. The explosive assembly has an actuation means for opening the first valve and a second valve that releases the microorganisms from the storage chamber to begin metabolizing the explosive material, when the explosive apparatus is joined with the bioremediating apparatus. If the explosive material fails to detonate, the explosive is remediated by the action of the microorganisms. Remediation includes both disabling of the explosive material and detoxification of the resulting chemical compositions. The valves utilized are either mechanical, and thus opened by the coupling of the bioremediating apparatus to the explosive apparatus, or comprised of a slowly effacing material, such as gelatin. A micro-scale form of a bioremediating apparatus includes microorganisms encapsulated in gelatin for disposition mixed in or contacting the explosive material.

69 Claims, 10 Drawing Sheets

U.S. PATENT DOCUMENTS

| | | | |
|---|---|---|---|
| 4,351,729 | 9/1982 | Witt | 210/603 |
| 4,845,034 | 7/1989 | Menger et al. | 435/167 |
| 4,929,552 | 5/1990 | Gold et al. . | |
| 4,961,381 | 10/1990 | McLaughlin | 102/319 |
| 5,011,614 | 4/1991 | Gresser et al. . | |
| 5,085,998 | 2/1992 | Lebron et al. | 435/262 |
| 5,120,441 | 6/1992 | Jackson et al. | 210/602 |
| 5,139,365 | 8/1992 | Chesner . | |
| 5,296,146 | 3/1994 | Jackson et al. | 210/602 |
| 5,314,821 | 5/1994 | Tyndall | 435/252.1 |
| 5,392,860 | 2/1995 | Ross | 166/376 |
| 5,414,198 | 5/1995 | Broadman et al. . | |
| 5,420,035 | 5/1995 | Tyndall | 435/252.1 |
| 5,449,618 | 9/1995 | Tyndall et al. . | |
| 5,455,173 | 10/1995 | Crawford et al. | 435/264 |
| 5,478,743 | 12/1995 | Perkins et al. . | |
| 5,484,730 | 1/1996 | Tyndall et al. | 435/264 |
| 5,511,482 | 4/1996 | DiPietropolo | 102/426 |
| 5,518,919 | 5/1996 | Tyndall | 435/262.5 |
| 5,543,324 | 8/1996 | Rajan et al. | 435/252.4 |
| 5,610,062 | 3/1997 | Tyndall | 435/252.4 |

SYSTEMS FOR BIOREMEDIATING EXPLOSIVES

RELATED APPLICATIONS

This application is a continuation-in-part application of U.S. patent application Ser. No. 560,074 that was filed on Nov. 17, 1995, now abandoned, and which discloses subject matter related to that disclosed in U.S. patent application Ser. No. 560,527 and U.S. patent application Ser. No. 560,102, both also filed on Nov. 17, 1995.

BACKGROUND OF THE INVENTION

1. The Field of the Invention

The present invention is directed to systems, apparatus, and methods for remediating explosives. More particularly, the present invention is directed to the remediation of explosives which have failed to detonate.

2. Background Art

Explosive charges are inherently dangerous in a number of respects.

Inadvertent detonation poses risks of severe personal injury or death, as well as of substantial property destruction and consequential losses. Explosive charges are, in addition, comprised of material substances, which even when not consolidated in shape capable of performing as a detonatable explosive charge, are nevertheless toxic and thus potentially injurious to human health and to complex as well as simple plant and animal life.

Explosive charges that are not securely stored in a supervised manner, or isolated from the environment and from indiscriminate access by human and animal life forms, thus present both safety and environmental hazards.

Such hazards are pointedly apparent where an explosive charge fails to detonate after the explosive charge has been installed for that purpose during activities pertaining to mining, construction, or to seismic surveying. Fortunately, installed explosive charges that do not detonate as planned are usually locatable and often recoverable through the expenditure of reasonable efforts and without safety risks to personnel. On the other hand, there do routinely arise circumstances in which undetonated explosive charges of this type are not recovered or simply cannot be recovered. Then, the risks are present that the undetonated explosive charge could at some subsequent time be detonated inadvertently or become a source of toxic environmental contaminants.

As an example, seismic survey data used to ascertain the nature of subsurface ground structures is routinely obtained by recording and analyzing shock waves that are propagated into the ground and produced by detonating explosive charges. The shock waves are then monitored during transmission through the ground. In this role, such seismic charges are usually utilized in large sets, installed as an array of individual seismic charges at widely dispersed locations. The seismic charges are interconnected with detonation equipment for remote detonation, either simultaneously or in sequence.

Seismic charges for such surveys can be detonated either above or below the surface of the ground. In either case, it is not uncommon that at least one of any set of such seismic charges does not detonate as intended. Such failures may be caused by defects in the explosive charge itself, by damage caused during installation, by faulty detonation equipment, or by the failure of personnel in the field to make effective interconnections between that detonation equipment and each seismic charge in the installed set.

When a seismic charge installed above the ground fails to detonate as intended, it is usually possible to locate and safely recover the undetonated seismic charge. Nonetheless, circumstances do exist where the detonation of a set of seismic charges installed above the ground dislocates one of the undetonated seismic charges in the set, directing that undetonated seismic charge into a terrain in which the charge cannot be located or cannot be recovered easily. Responsible seismic crews naturally are trained to exercise all reasonable efforts to recover undetonated seismic charges that are located on the surface of the ground, but even the most rigorously indoctrinated and enthusiastic seismic personnel cannot guarantee that all undetonated seismic charges installed above the ground are ultimately recovered.

Aside from the human factor involved, the intervention of severe weather conditions, such as sandstorms, blizzards, tornadoes, or hurricanes, can impede efforts to recover undetonated seismic explosives. Some such weather conditions offer the prospect of even altering the terrain, thereby burying the undetonated seismic charge temporarily or for a substantial duration. Floods can cover the seismic survey site, removing or obscuring undetonated seismic charges. In the extreme, geological surface changes, such as mudslides, rockfalls, and fissures caused by earthquakes, by heavy weather, or even by seismic survey activity itself, can preclude the recovery of undetonated seismic charges, and even obscure the understanding that any seismic charge has failed to detonate.

The safety risks and environmental hazards posed by loose, undetonated explosive charges will be present where any undetonated seismic charge remains unrecovered after the detonation of the set of seismic charges of which it was a part.

The likelihood that an undetonated seismic charge will be abandoned is greatest, however, relative to the conduct of seismic survey activity based on the detonation of seismic charges installed below the surface of the ground. In such sub-surface seismic detonation activity, a series of deep boreholes are drilled into the earth or rock at predetermined locations that are intended to maximize the data to be derived from the shock waves promulgated from the detonation of the seismic charges. A seismic charge is placed at the bottom of each borehole and then shut in the borehole in a relatively permanent manner using a concrete or a sealing compound, such as bentonite. The balance of the borehole is then backfilled with loose soil and rock; a process which alone accounts for the majority of failed seismic detonations. Backfill materials have an understandable tendency to break the detonating cord that interconnects the installed seismic charge at the bottom of the borehole with detonating equipment located above the ground. If a seismic charge installed below the ground fails to detonate, the easy removal of the undetonated seismic charge is seriously impeded by yards of backfill and the cured concrete or sealing compound in which the seismic charge was embedded at the bottom of the original borehole. Removing such an installed seismic charge by reexcavating the original borehole or by digging around the original borehole to avoid the sealing compound is extremely laborious and time consuming, potentially unsafe, and in many circumstances virtually impossible.

Thus, in conducting seismic survey activities, particularly seismic survey activities involving the detonation of seismic charges below the surface of the ground, undetonated seismic charges are regularly abandoned in the field. Frequently, even the precise location of undetonated seismic charges cannot be pinpointed. The risks from undetonated explosive charges installed in the ground endure for a substantial time, usually exceeding the durability of ground surface warning signs, fencing, or the continued possession and control of access to the sine by an original owner. Eventually, the pressure of human population growth may render the site attractive for civil or industrial activities that would not be consistent with buried undetonated explosive charges.

The associated dangers include first that of an accidental detonation at some future time. Less dramatic, but certainly of longer duration, are risks presented by the material substance of those undetonated charges. Once released from the confines of the casing of an explosive assembly, the explosive material therein may cease to present any risk of explosion. This type of release of explosive materials can occur through corrosion of the casing through the action of ground water, the fracture of the casing during careless installation, or the shifting of the ground structure at the location at which the undetonated seismic charge was abandoned. In due course, the prolonged effect of these forces in combination with surface erosion or subsurface fluid migration can disburse over a large area the material of a fractured explosive charge. That material constitutes a toxic environmental contaminant. Even if detected, extensive remedial activities will be required, first to contain, and then, if possible, to neutralize the pollutants.

Nonetheless, no practical methods exist for reliably remediating the risks posed by undetonated explosive charges, particularly where those undetonated explosive charges are originally installed below the surface of the ground.

SUMMARY OF THE INVENTION

It is thus the broad object of the present invention to protect public health and safely from risks arising from incidents of abandoned undetonated explosive charges.

Accordingly, it is a related object of the present invention to eliminate the possibility of detonation of abandoned explosive charges.

It is a complementary object of the present invention to reduce the likelihood that abandoned undetonated explosive charges will contribute to environmental pollution.

Thus, it is a specific object of the present invention to provide apparatus, systems, and methods for remediating in situ any installed explosive charge that fails to detonate as intended.

It is a particular object of the present invention to provide such apparatus, systems; and methods as are capable of reliably and safely remediating an undetonated explosive charge abandoned in the ground.

Yet a further object of the present invention is to provide such apparatus, systems, and methods as are capable of remediating an undetonated explosive charge, even if the location of the explosive charge cannot be ascertained with any degree of certainty.

These and other objects and features of the present invention will become more fully apparent from the following description and appended claims, or will be appreciated by the practice of the invention.

To achieve the foregoing objects, and in accordance with the invention as embodied and broadly described herein, apparatus, systems, and methods are provided that remediate in situ an undetonated explosive utilizing the biological activity of microorganisms.

In one form, an apparatus incorporating teachings of the present invention includes a bioremediation apparatus in combination with an explosive material. The bioremediation apparatus includes a storage means for releasably containing at least one type of microorganism capable of degrading explosive materials. Stored distinctly therefrom in the bioremediation apparatus is a reservoir means for releasably containing a solution intended to be mixed with the microorganisms. The storage means is positioned proximate the reservoir means, usually in a relationship that is below the reservoir means in the anticipated installed orientation of the inventive apparatus.

The bioremediation apparatus further includes a first valve means for delivering the solution from the reservoir means to the microorganisms in a storage means. Doing so causes hydration of the microorganisms. This occurs when a first valve means is opened. The first valve means is at least partially disposed within the reservoir means.

Additionally, the bioremediation apparatus of the present invention comprises a second valve means for delivering hydrated microorganisms to an associated, undetonated explosive material. The second valve means is operably linked to the first valve means and is at least partially disposed within the storage means.

The bioremediation apparatus is coupled in one embodiment of the present invention with an explosive apparatus that has an actuation means for opening the first valve means and the second valve means upon being coupled thereto. If the explosive material in the explosive apparatus fails to detonate, the explosive material will eventually be remediated by the action of the microorganisms released from the associated storage means.

Ideally, the remediation occurs in two respects. The explosive is disabled from inadvertent detonation. Subsequently, the material composition of the explosive material is rendered nontoxic.

In another embodiment of the invention, microorganisms are releasably contained by gelatin, a substance that is self-effacing when contacted by microorganisms under favorable conditions. For example, gelatin may be used to fabricate the first valve means that retains solution in the reservoir means of the bioremediation apparatus or the second valve means that retains the microorganisms in the storage means of the bioremediation apparatus. Alternatively, gelatin capsules containing microorganisms can be placed in the storage means in the bioremediation apparatus, applied directly to the exterior of the explosive material, or intermixed directly with the explosive material in an explosive apparatus. In yet another embodiment, microorganisms are placed directly in contact with an explosive material. For example, the microorganisms can be applied directly to the exterior of the explosive material or can be intermixed with the explosive material in an explosive apparatus.

BRIEF DESCRIPTION OF THE DRAWINGS

In order that the manner in which the above-recited and other advantages and objects of the invention are obtained, a more particular description of the invention briefly described above will be rendered by reference to specific embodiments thereof, which are illustrated in the appended drawings. Understanding that these drawings depict only typical embodiments of the invention and are not therefore to be considered to be limiting of the scope of the invention, the present invention will be described and explained with additional specificity and detail through the use of the accompanying drawings in which.

DETAILED DESCRIPTION OF THE PREFERRED EMBODIMENTS

Figure 1:
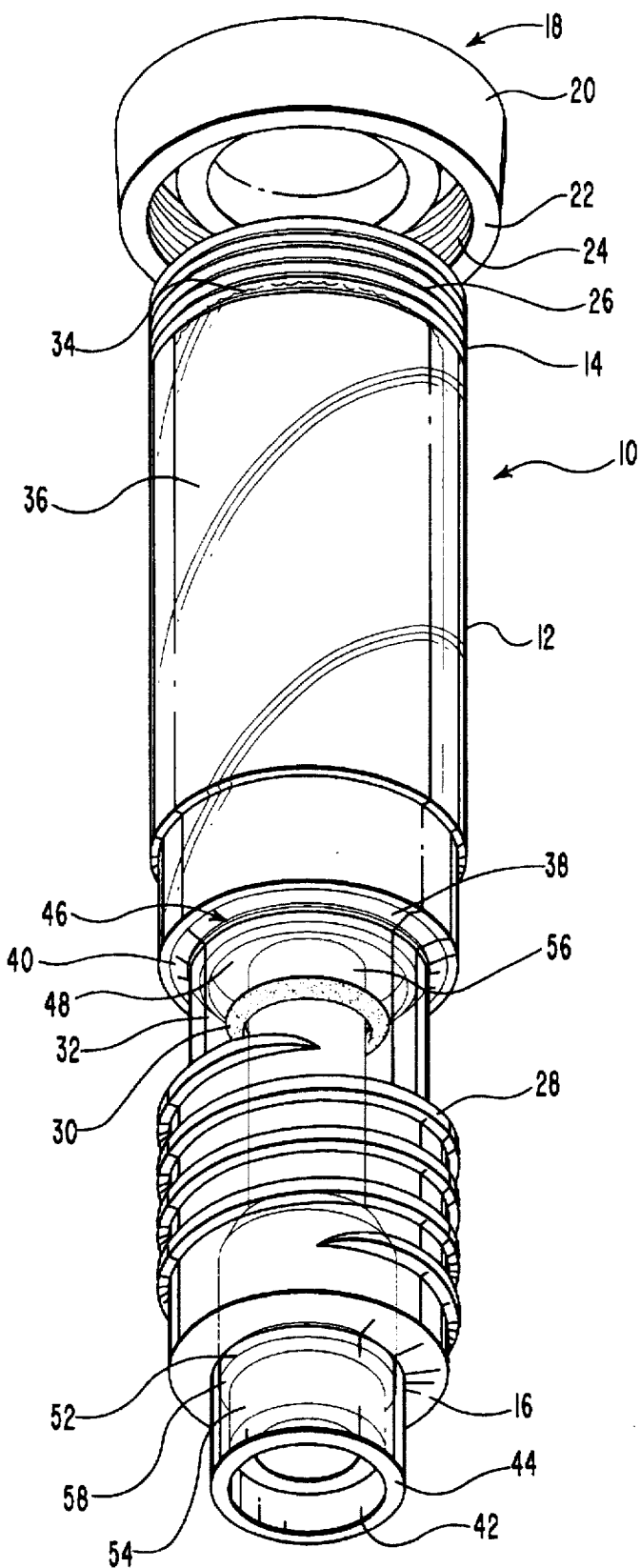
FIG. 1 is a perspective view of a first embodiment of a bioremediation apparatus incorporating teachings of the present invention.
Figure 2:
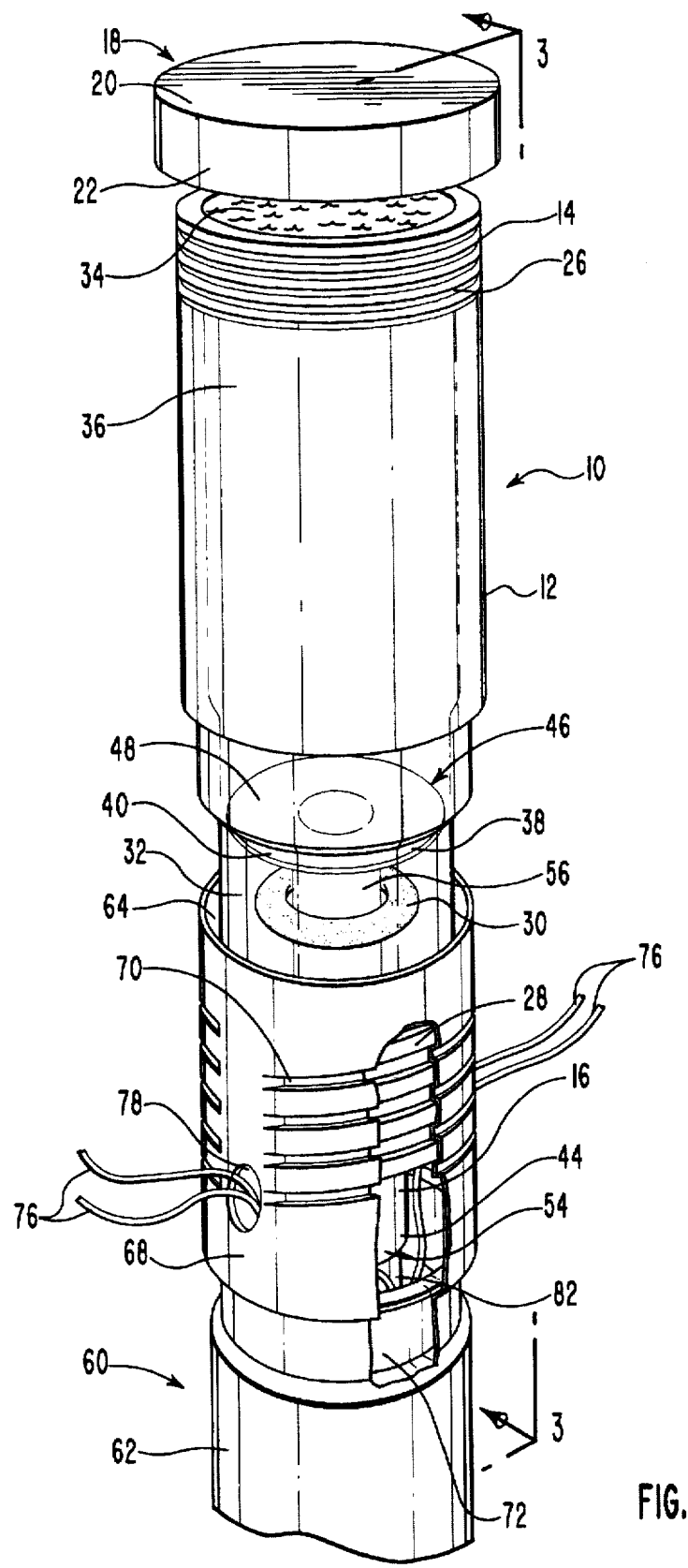
FIG. 2 is a perspective view in partial break-away of the bioremediation apparatus of FIG. 1 in the process of being coupled with an explosive apparatus in accordance with teachings of the present invention.

The present invention pertains to systems, apparatus, and methods for the in situ remediating of undetonated explosive charges. The methodology employs at least one type of microorganism that is capable of digesting an explosive material.

According to the teachings of the present invention, an explosive charge to be installed, for example by being buried in the ground, is so housed in a casing with the microorganisms. If the explosive charge fails to detonate, the explosive charge can then reliably be left undisturbed; and the microorganisms will digest or degrade the explosive material involved. Preferably, the explosive will be thereby both disabled from detonation and detoxified.

The terms "remediate" and "remediation" are used in the specification and the appended claims to refer generally to the conversion or transformation of an explosive material which is detonatable by shock or heat into a different chemical material which is less explosive or nonexplosive. The terms "bioremediate" and "bioremediation" are used to refer to remediation effected by the action of microorganisms. The present invention is thus one intended to bioremediate explosive materials.

The present invention has demonstrated an immediate utility relative to highly explosive materials, such as trinitrotoluene (TNT), pentaerythritol tetranitrate (PETN); cyclotrimethylene trinitramine (RDX), and cyclotetramethylene tetranitramine (HMX). These are typically utilized in seismic charges.

The term "bioremediable explosive" is used in the specification and the appended claims to refer to any explosive material which can be converted into a less explosive or nonexplosive material by the action of microorganisms, whether or not such microorganisms are explicitly disclosed herein. The highly explosive materials listed above are thus bioremediable explosives, since it has been demonstrated that at least the examples of microorganisms disclosed herein are capable of converting those high energy explosive materials into less explosive or nonexplosive materials.

Currently, on the basis exclusively of the examples of microorganisms disclosed herein; known bioremediative explosives include at least explosives which are classified as organic nitroaromatics, organic nitramines, or organic nitric esters. Examples of organic nitroaromatics include TNT, hexanitrostilbene (HNS), hexanitroazobenzene (NAB), diaminotrinitrobenzene (DATB), and triaminotrinitrobenzene (TATB). Examples of organic nitramines include RDX, HMX, nitroguanidine (NQ), and 2,4,6-trinitrophenylmethylnitramine (tetryl). Examples of organic nitric esters include PETN, nitroglycerine, and ethylene glycol dinitrate.

In one embodiment of the present invention, highly explosive materials, such as TNT and PETN, are converted through the action of microorganisms into less explosive materials that include aromatic compounds, such as benzene or derivatives of benzenes such as toluene. These aromatic compounds are intermediate chemicals in the full transformation of organic nitroaromatics into materials such as biomass and chemicals such as $CO_2$ and $N_2$. Optimally, the highly explosive materials are reduced according to the teachings of the present invention, first into less explosive intermediate chemicals or nonexplosive products. These intermediate chemicals can then be further transformed as needed into constituents which are either less explosive, less toxic, or less carcinogenic than the intermediate chemicals. The final product resulting from the metabolizing action of the microorganisms will thus include any number of combinations of elements that originated in the explosive material as constituted before the start of the bioremediation process.

The microorganisms comprise a first type of microorganisms that disable or deactivate the explosive material by degrading the explosive material into less explosive materials or nonexplosive materials. The microorganisms may also further comprise a second type of microorganisms that further bioremediate any intermediate chemicals resulting from the bioremediation action of the first type of microorganisms to fully bioremediate the explosive material into nonexplosive materials.

Although any type of microorganisms capable of converting explosive material into less harmful chemicals is considered to be within the scope of the present invention, examples of microorganisms that have been demonstrated to exhibit that capacity include the group consisting of Pseudomonas spp., Escherichia coli, Morganella morganii, Rhodococcus spp., Comamonas spp., and denitrifying bacteria. It is within the scope of the present invention to use any combination of these particular microorganisms, or of any other microorganisms that are determined to be capable of bioremediating explosive materials. Suitable Pseudomonas spp. microorganisms include microorganisms in the group consisting of aeruginosa, fluorescens, acidovorans, mendocina, cepacia, and an unidentified type.

The present invention thus utilizes any of numerous different selections of microorganisms capable of degrading explosive materials in any of various relative quantities. Each of these various selections of microorganisms will for convenience hereinafter and in the appended claims be referred to as a "microorganism consortium." In such a microorganism consortium, one type of microorganism can advantageously reduce the explosive material to a particular intermediate chemical, such as benzene, while that type or another type of microorganism may then further reduce the benzene to carbon chains or to individual carbon atoms. In one presently preferred embodiment, such a microorganism consortium utilizes all or some of various of the microorganisms belonging to Pseudomonas spp., *Escherichia coli*, *Morganella morganii*, Rhodococcus spp., Comamonas spp., and denitrifying bacteria.

A consortium of microorganisms within the scope of the present invention has been deposited for the purposes of this disclosure with the American Type Culture Collection (hereinafter "ATCC") in accordance with the provisions of the Budapest Treaty on the International Recognition of the Deposit Microorganisms for the Purpose of Patent Procedure. The deposited consortium of microorganisms was assigned ATCC Designation No. 55784. For purposes of this disclosure, the microorganism consortium deposited with the ATCC and designated ATCC Designation No. 55784 is hereby incorporated by reference.

The microorganism consortium deposited with the ATCC was obtained from Richards Industrial Microbiology Laboratories, Inc. (hereinafter "RIML") located at 55 East Center, Pleasant Grove, Utah 84062 U.S.A. The microorganism consortium is identified at RIML by Product No. RL-247. Accordingly, microorganisms sold as RL-247 by RIML under the tradename RL-247 and assigned ATCC Designation No. 55784 are considered to be within the scope of the invention disclosed herein, whether or not constituent microorganisms therein are explicitly identified to any degree herein.

The microorganisms of the microorganism consortium are chosen for having a demonstrated ability to metabolize and degrade explosive materials in any way that contributes to the disabling of the explosive material or to the detoxification of the chemical components thereof. If microorganisms are selected that are both aerobic and anaerobic, bioremediation will occur in shallow and exposed surface locations, as well as in deep explosive boreholes. Ideally, the microorganisms selected for the microorganism consortium should be nonpathogenic and surfactant-producing, as this enhances the digestive action of the microorganism colony.

In one embodiment of a microorganism consortium chosen according to the teachings of the present invention, the Pseudomonas spp. are selected from the group consisting of aeruginosa, flourescens, acidovorans, mendocina, and cepacia. Any microorganisms of Pseudomonas spp. other than the microorganisms identified above are considered to be within the scope of the invention disclosed herein, provided that such microorganisms perform any of the functions described above having utility in the remediating of an explosive charge. Correspondingly, any microorganism is considered to be within the scope of the invention disclosed herein, provided the microorganism exhibits any utility relative to the bioremediating of explosive materials.

Thus, the disclosure and incorporation herein of the microorganism consortium assigned ATCC Designation No. 55784 or the disclosure of the microorganism consortium available from RIML under the tradename RL-247, are but examples of microorganisms consortiums within the teachings of the present invention and are not limiting of the microorganisms than may be selected for inclusion in a microorganism consortium according to the teachings of the present invention.

A first embodiment of an apparatus employing principles of the present invention is illustrated in FIG. 1 as an explosive bioremediation apparatus 10. Bioremediation apparatus 10 includes a casing 12 having a top end 14 and a bottom end 16. Casing 12 is preferably formed from a material which is water resistant and is capable of withstanding extremes of temperature.

A cap 18 is inserted into top end 14 of casing 12. Cap 18 is preferably formed from a durable material that will withstand being driven down a borehole with a tamping pole. Cap 18 includes a cap top 20 and an external cap member 22 integrally extending from cap top 20 and having cap threads 24. Cap 18 is secured about top end 14 of casing 12 by engaging cap threads 24 which end threads 26 that are formed on the exterior of top end 14. Cap 18 may include an internal cap member with an O-ring or a foam seal so configured and positioned as to engage top end 14 of casing 12. This increases the security of the seal produced.

Cap 18 is but one example of a structure capable of functioning as a cap means for sealing the top end of a casing, such as casing 12. Another example of a structure capable of performing the function of a cap means according to the teachings of the present invention would be a casing without any external cap member, but rather having an internal cap member that is inserted into top end 14. Alternatively, bioremediation apparatus 10 could be provided with a structure that performs the foundation of such a cap means but is integrally formed with casing 12. Any such cap structure that is integrally formed with casing 12 from a plastic material should be constructed to withstand the impacts and pressure encountered in being pushed down a borehole.

Bioremediation apparatus 10 is configured at bottom end 16 of casing 12 for coupling with an explosive apparatus shown and discussed subsequently in relation to FIGS. 2–6 as housing a bioremediatable explosive material. Bioremediation apparatus 10 also has casing threads 28 on casing 12 that cooperatively engage correspondingly configured threads on the explosive apparatus to effect the intended coupling.

According to teachings of the present invention, microorganisms 30 capable of degrading explosive materials are stored in a moist condition in a storage means for releasably containing microorganisms. By way of example and not limitation, such a storage means within the scope of the present invention can take the form of a storage chamber 32 having sidewalls defined by casing 12. As shown in FIGS. 1–5, microorganisms 30 can be positioned on a ring formed from starch and flour, bran, or another similar material. Storing microorganisms 30 in a moist condition in storage chamber 32 increases the shelf life of microorganisms 30. Microorganisms 30 are not hydrated until bioremediation apparatus 10 is actually coupled with an explosive apparatus which is preferably in the field at the time of the intended detonation of the charge in that explosive apparatus. In addition to a ring configuration, microorganisms 30 can be positioned in contact with materials such as starch, flour, or bran assuming any other arrangement. Microorganisms 30 can also be placed in storage chamber 32 without nutrients, such as starch, flour or bran, so long as bioremediation apparatus 10 is intended to be used within the expected lifetime of the microorganisms 30 if unnourished.

Microorganisms 30 are hydrated by a solution 34 stored in a reservoir means for releasably containing solution. Solution 34 may be water or a nutrient medium that can feed microorganisms 30, but solution 34 is resistant to freezing at ambient temperatures. By way of example and not limitation, a reservoir means within the scope of the present invention can take the form of a reservoir chamber 36. Reservoir chamber 36 has sidewalls defined by the interior of casing 12 and a top defined by cap 18. Reservoir chamber 36 also includes a solution passage 38 defined by the interior of a neck 40. Neck 40 is an integral portion of casing 12 and has a diameter that tapers radially inwardly from the outer diameter of the sidewalls of reservoir chamber 36 to a smaller diameter, as observed to best advantage in FIG. 3.

Preferably, storage chamber 32 is positioned below reservoir chamber 36 in the anticipated orientation of bioremediation apparatus 10 when coupled to and installed with explosive apparatus 60. Storage chamber 32 is capable of communication with reservoir chamber 36 through solution passage 38. Storage chamber 32 is provided with a bioremediation outlet 42 that is formed through bottom end 16 of casing 12 and through a sleeve member 44 which protrudes from bottom end 16 of casing 12. Accordingly, bioremediation outlet 42 is a portal or opening through casing 12 that is in communication with storage chamber 32.

Microorganisms 30 are hydrated by solution 34 upon the opening of a first valve means for delivering solution 34 from reservoir chamber 36 to storage chamber 32. By way of example and not limitation, a first valve means according to the teachings of the present invention can take the form of a first valve 46 which comprises the interior of neck 40 and a first valve member 48. A tapered end 50 is formed around the perimeter of first valve member 48 corresponding in dimension to the interior of neck 40. The cooperation of these structures forms a seal within solution passage 38.

Figure 3:
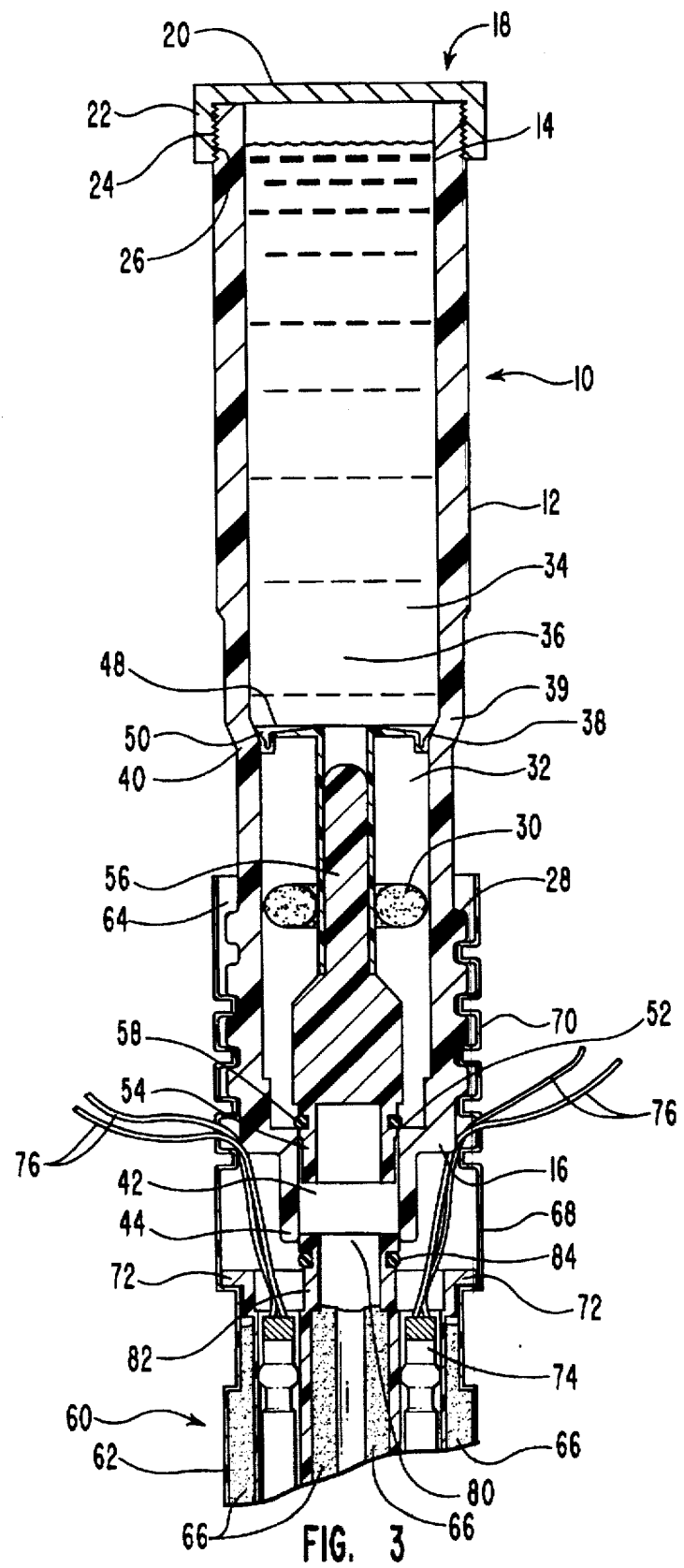
FIG. 3 is a cross-sectional elevation view of the bioremediation apparatus and the explosive apparatus illustrated in FIG. 2 taken along section line 3—3 shown therein.

When first valve 46 is closed as shown in FIG. 3, first valve 46 is at least partially disposed within reservoir chamber 36. More particularly, when first valve 46 is closed, first valve 46 is positioned between reservoir chamber 36 and storage chamber 32 and within solution passage 38 with first valve member 48 defining the bottom of reservoir chamber 36 and the top of storage chamber 32. The seal formed within solution passage 38 by first valve 46 thereby retains solution 34 in reservoir chamber 36 until first valve 46 is opened.

Once hydrated, microorganisms 30 flow out of storage chamber 32 upon the opening of a second valve means for delivering hydrated microorganisms to an explosive material in an explosive apparatus. By way of example and not limitation, a second valve means according to the teachings of the present invention can take the form of a second valve 52 which includes a second valve member 54 in combination with sleeve member 44. Second valve 52 defines the bottom of storage chamber 32 and is the lower end of a valve connector 56 that extends through bioremediation outlet 42 in sleeve member 44. Valve connector 56 has an upper end that is connected to first valve member 48.

When second valve 52 is closed as shown in FIG. 3, second valve 52 is at least partially disposed within storage chamber 32. More particularly, when closed, second valve 52 is positioned at the bottom of storage chamber 32 within bioremediation outlet 42. Second valve member 54 forms a seal with sleeve member 44 in bioremediation outlet 42, thereby to retain hydrated microorganisms 30 in storage chamber 32 until second valve 52 is opened. The security of the seal is increased by a valve O-ring 58, which encircles second valve member 54.

Valve connector 56 can best be seen in FIG. 3 to connect first valve member 48 and second valve member 54. The length of valve connector 56 is selected to enable first valve 46 and second valve 52 to open and close according to a predetermined timing relationship. Thus, first valve 46, second valve 52, and valve connector 56 can be configured to effect the simultaneous opening or actuation of first valve 46 and second valve 52. Alternatively, first valve 46, second valve 52, and valve connector 56 can be designed to actuate one of the valves in a delayed manner, after the other valve has been actuated. It may be desirable for example, to allow solution 34 to fully hydrate microorganisms 30 by opening first valve 46, and only thereafter to open second valve 52.

When microorganisms 30 and solution 34 are securely sealed in separate spaces as shown in FIG. 3, bioremediation apparatus 10 can be shipped and stored for long periods without any significant decrease in the bioremediating effectiveness thereof. The configuration of bioremediation apparatus 10 is designed for easy combination with a conventional explosive, such as a seismic booster.

FIGS. 2 and 3 depict bioremediation apparatus 10 in the process of being coupled with an explosive apparatus 60. FIG. 2 is a perspective view, and FIG. 3 is a cross-sectional view taken along section line 3—3 of FIG. 2. As best illustrated in FIG. 3, first valve member 48 and second valve member 54 remain in closed positions when bioremediation apparatus 10 is initially threaded into explosive apparatus 60.

Explosive apparatus 60 comprises a shell 62 having an open end 64 and an explosive material 66 housed within shell 62. The interior of shell 62 is provided with shell threads 70 near open end 64. These cooperate with correspondingly configured casing threads 28 on bioremediation apparatus 10. Shell 62 can be formed from distinct components or as an integral structure as shown.

The combination of casing threads 28 and shell threads 70 together serve as an example of a coupling means for coupling a bioremediation apparatus according to the teachings of the present invention with an explosive apparatus, such as explosive apparatus 60. In the embodiment illustrated, the function of such a coupling means is performed by an extension of casing 12 of bioremediation apparatus 10 and an extension of shell 62 of explosive apparatus 60. Alternatively configured structures can, however, perform the function of such a coupling means.

For example, a wedge fit can be effected between bioremediation apparatus 10 and explosive apparatus 60 using respective angled male and female parts attached, respectively, to each. While the coupling means is primarily a mechanism to join bioremediation apparatus 10 and explosive apparatus 60, it is within the teachings of the present invention to provide structures that prevent bioremediation apparatus 10 and explosive apparatus 60 from being unintentionally separated, thereby performing the function of a locking means for securing bioremediation apparatus 10 and explosive apparatus 60 against the disengagement of the coupling together thereof.

Explosive apparatus 60 further comprises a capwell 72 positioned in open end 64 to receive detonators 74. Detonators 74 are in turn electrically connected by wires 76 to the exterior of shell 62 through wire access openings 78 shown in FIG. 2. A bioremediation portal 80 formed through capwell 72 communicates with explosive material 66 to afford access by hydrated microorganisms 30 from bioremediation outlet 42 to explosive material 66. A portal member 82 extends upwardly as shown in FIG. 3 from the center of capwell 72, encircling and defining on the interior thereof bioremediation portal 80. A portal O-ring 84 encircles portal member 82 to provide a fluid seal between sleeve member 44 and portal member 82 when explosive bioremediation apparatus 10 is coupled with explosive apparatus 60.

Figure 4:
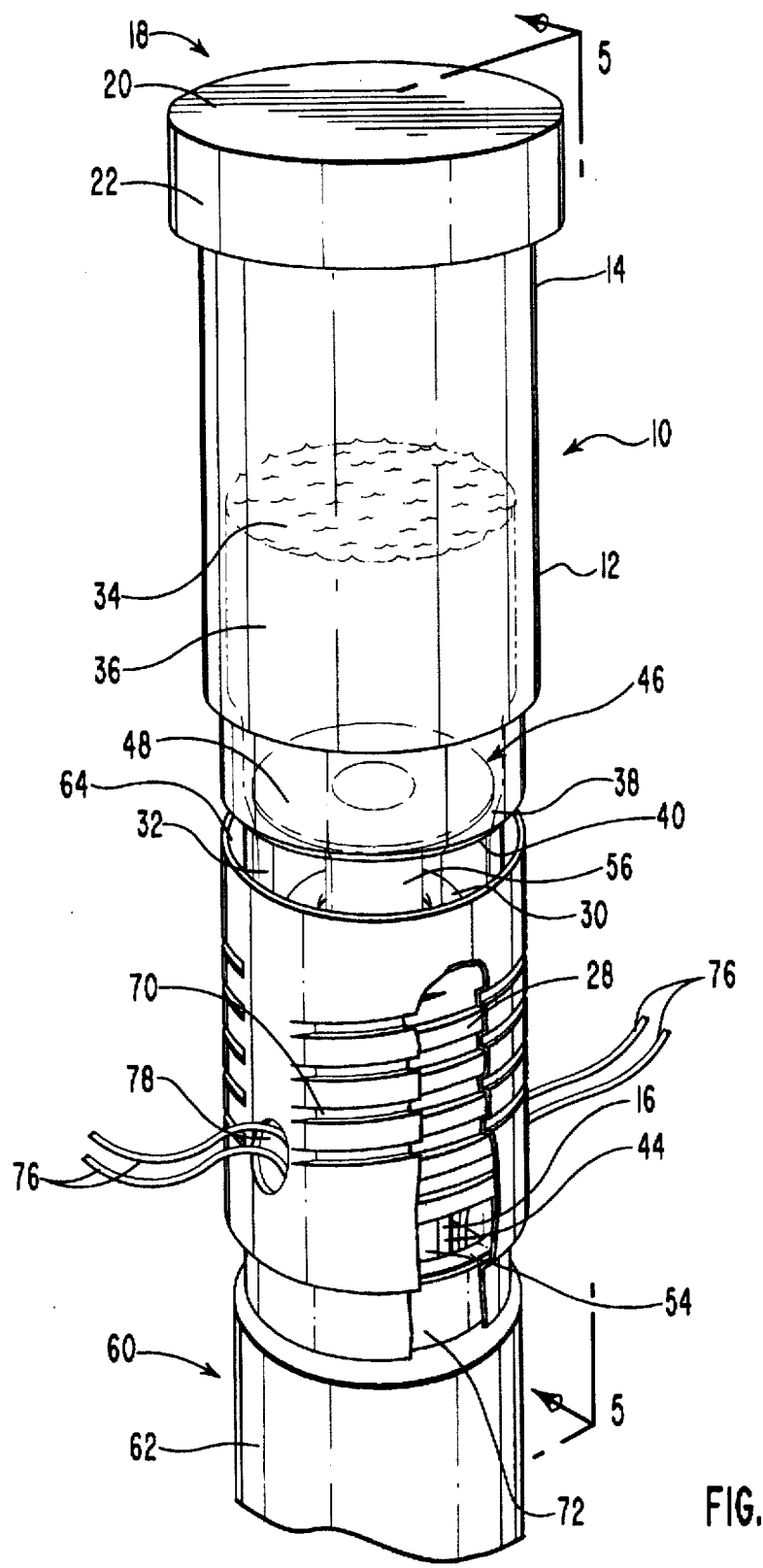
FIG. 4 is a perspective view in partial break-away of the bioremediation apparatus and the explosive apparatus of FIG. 2 immediately upon becoming fully coupled.
Figure 5:
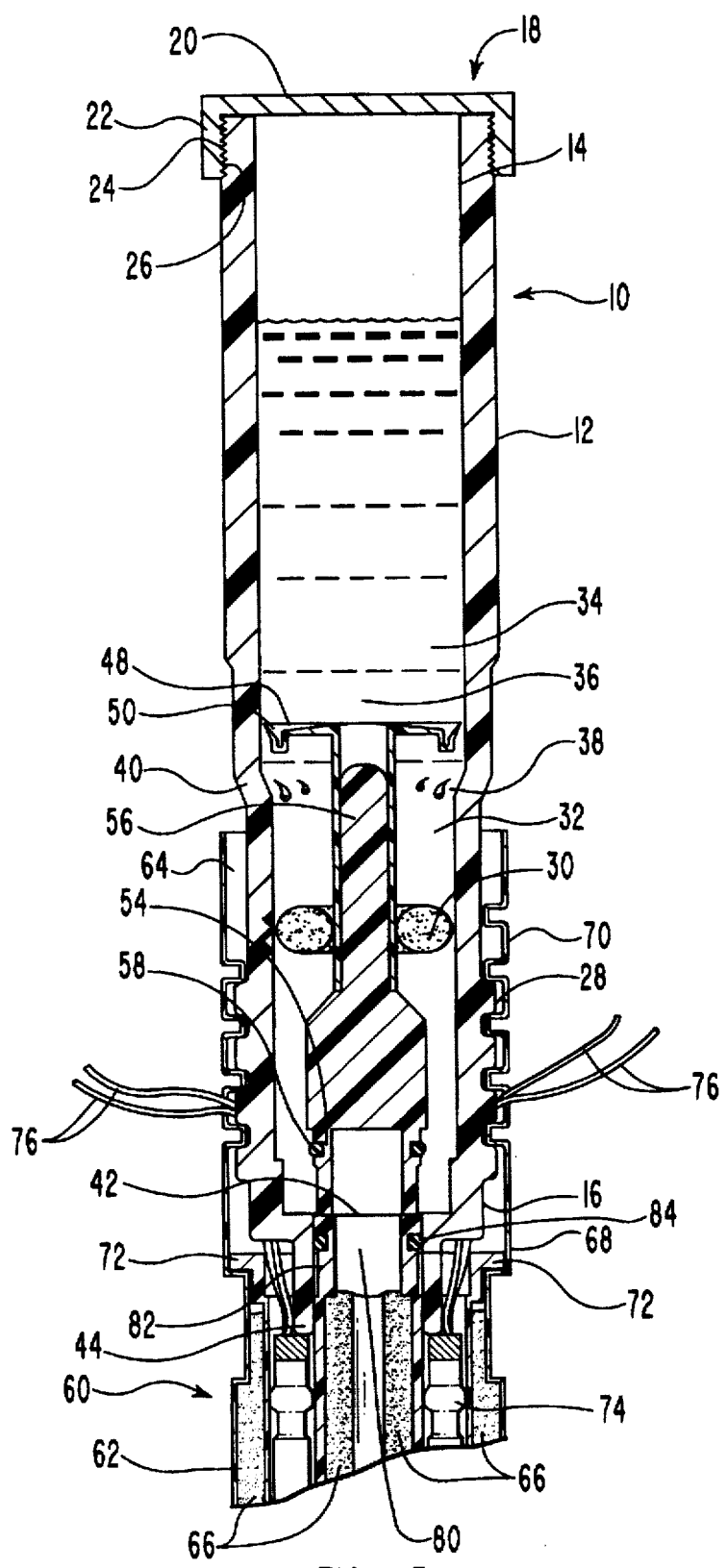
FIG. 5 is a cross-sectional elevation view of the bioremediation apparatus and the explosive apparatus illustrated in FIG. 4 taken along section line 5—5 shown therein.

FIGS. 4 and 5 depict bioremediation apparatus 10 immediately after becoming completely coupled with explosive apparatus 60. FIG. 4 is a perspective view, and FIG. 5 is a cross-sectional view taken along section line 5—5 of FIG. 4. FIG. 5 illustrates to best advantage that as a result of the coupling of bioremediation apparatus 10 with explosive apparatus 60, first valve 46 and second valve 52 have been opened. Solution 34 is shown being delivered by gravity from reservoir chamber 36 through solution passage 38 to storage chamber 32.

As bioremediation apparatus 10 is being coupled with explosive apparatus 60, sleeve member 44 and portal member 82 advance toward each other until portal member 82 is positioned within sleeve member 44. A fluid seal is formed between sleeve member 44 and portal member 82 by portal O-ring 84. The advancement of bioremediation apparatus 10 brings portal member 82 into abutment against second valve member 54. As valve connector 56 effects a rigid interconnected relationship between second valve member 54 and first valve member 48, further advancement of bioremediation apparatus 10 into and toward explosive apparatus 60 forces second valve member 54 out of bioremediation outlet 42 and forces first valve member 48 out of solution passage 38.

Sleeve member 44, second valve member 54, and portal member 82 can have any lengths that enable first valve 46 and second valve 52 to be opened. In the embodiment shown in FIGS. 5 and 6, portal member 82 and second valve member 54 each have a length that is less than the length of sleeve member 44, and the length of portal member 82 is approximately equal to or greater than the length of second valve member 54.

Figure 6:
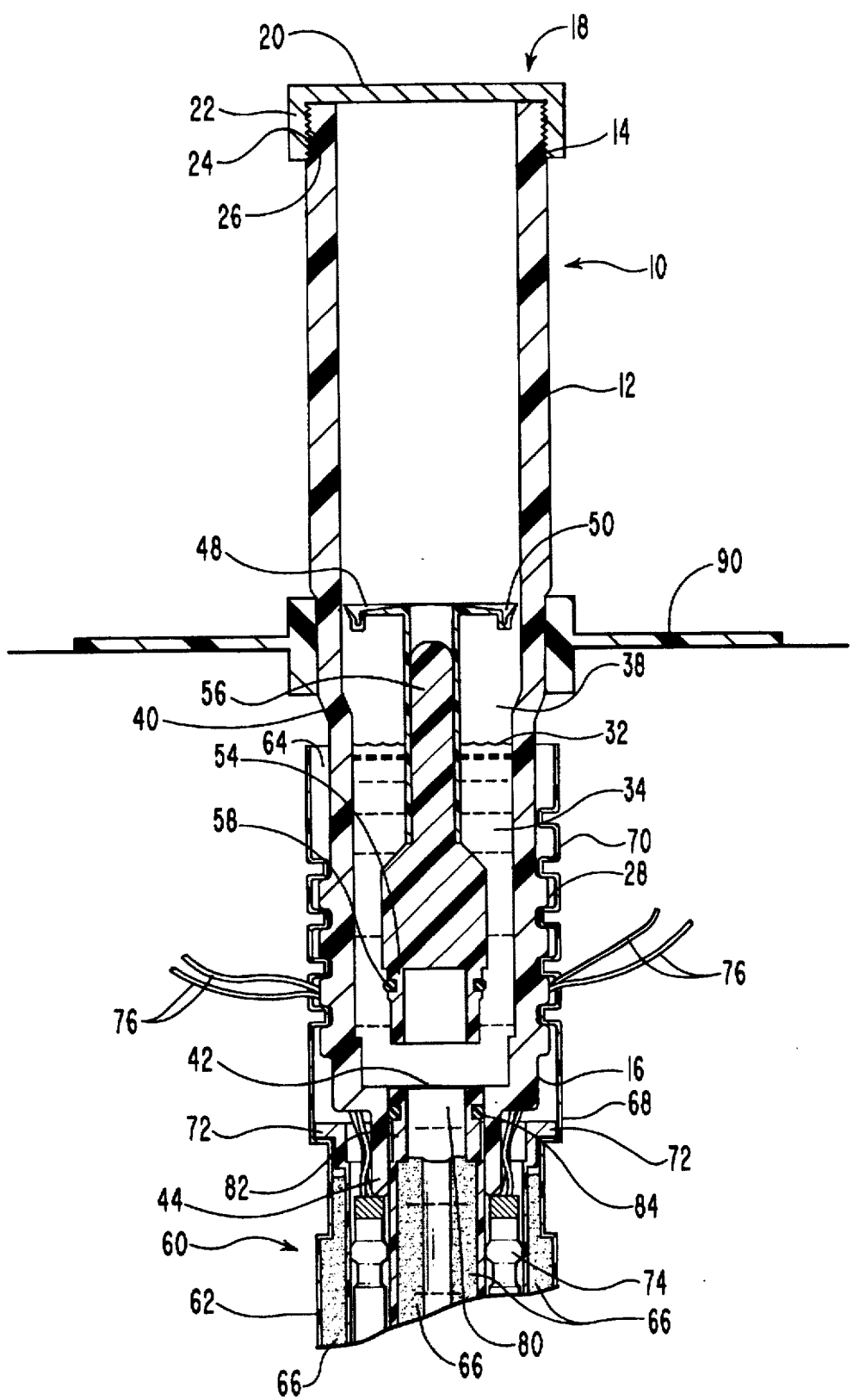
FIG. 6 is a cross-sectional elevation view like that of FIG. 5 illustrating the bioremediation apparatus and explosive apparatus in FIG. 4 at a time subsequent to that illustrated in FIG. 5 at which the explosive material in the explosive apparatus illustrated is contacted by hydrated microorganisms.

Forcing second valve member 54 and first valve member 48 upward within casing 12 opens a flow path than permits hydrated microorganisms 30 to contact explosive material 66 through bioremediation portal 80 as shown in FIG. 6.

First valve member 48, second valve member 54, and valve connector 56 form a divider which is preferably formed at least partially from a lightweight material such as polyethylene. The divider in this manner preferably has a lower density than water. This enables the divider to float to the top of the solution of microorganisms as shown in FIG. 6 after the solution has flowed into contact with explosive material 66.

The divider formed by first valve member 48, second valve member 54, and valve connector 56 is an example of a divider means for releasing microorganisms to an explosive material according to the teachings of the present invention. In an alternative embodiment, the divider means can take the form of a valve means for delivering the hydrated microorganisms from a storage means to an explosive material in a storage chamber of an explosive apparatus. The microorganisms are in a moist condition or in solution. Such an alternative embodiment accordingly utilizes but a single chamber and a single valve.

Portal member 82 is an example of an actuation means for initiating contact between hydrated microorganisms and an explosive material by opening first valve 46 and second valve 52. In an alternative embodiment, portal member 82 has a length greater than sleeve member 44, thereby rendering unnecessary any second valve member extending within sleeve member 44 to align portal member 82 for contact with the second valve member. In an additional alternative embodiment, second valve 52 is configured similarly to first valve 46. In this additional alternative embodiment, second valve 52 has a valve member within bioremediation outlet 42 that does not extend downward, and there is no sleeve member to provide alignment for portal member 82 in contacting the valve member to actuate second valve 52. Any structure capable of initiating access by hydrated microorganisms 30 to explosive material 66 is within the scope of the actuation means of the present invention.

The actuation means and the coupling means are taken together exemplary of a contact means for initiating and maintaining contact between hydrated microorganisms and an explosive material.

The coupling of bioremediation apparatus 10 with explosive apparatus 60 forms a system for in situ bioremediating of an explosive material. The system can be lowered into or driven down a borehole by contacting cap 18 with a tamping pole. Additionally, an anchor member 90 shown only in FIG. 6 can be positioned about casing 12 to maintain the system in the upright position illustrated during installation of the system at the bottom of a borehole. Anchor member 90 is preferably a disc circumferentially encircling casing 12 and extending perpendicularly outwardly therefrom. The longitudinal position of anchor member 90 along the length of casing 12 is maintained as shown in FIG. 6 by the increase in the outer diameter of casing 12 above anchor member 90.

If desired, once the system is positioned and sealed in the bottom of a borehole, the balance of the extent of the borehole is loaded with a backfill of inert matter. The backfill process is one of the primary causes of the failure of installed explosives to detonate. In the process, wires 76 are often broken or disconnected from detonators 74, so that detonation cannot occur. When this happens, the digestion of explosive material 66 by microorganisms 30 will proceed in due course. Eventually, explosive material 66 will be reduced to nonexplosive and non-toxic materials that are neither detonatable by any activities in the vicinity, nor are an environmental contaminant.

Over time, by exposing an undetonated charge to the microorganisms, the entirety of the explosive material of the charge is reduced to a substance that cannot be detonated. In the illustrated embodiments of the present invention, the digestive activity of microorganisms 30 disarms explosive material 66 by first attacking the area around the capwell end of the explosive apparatus. This is where detonation is actually initiated. There is, however, is no overall detrimental effect on the ability of an explosive charge to be detonated immediately after being initially contacted by bioremediating microorganisms. The initial activity of the microorganisms in the vicinity of the capwell does prevent accidental detonation of the explosive charge caused by way of any structure, such as one of wires 76: that was originally coupled to the explosive charge through the cap wall.

The time period required for the microorganisms to first disable an explosive, and then to fully remediate a given quantity of intermediate chemical materials depends on the amount and type of explosive material used, as well as the composition of microorganism consortium used therewith. Depending on design, relative concentrations of the explosive, the time required can be days, weeks, months, or years.

Figure 7:
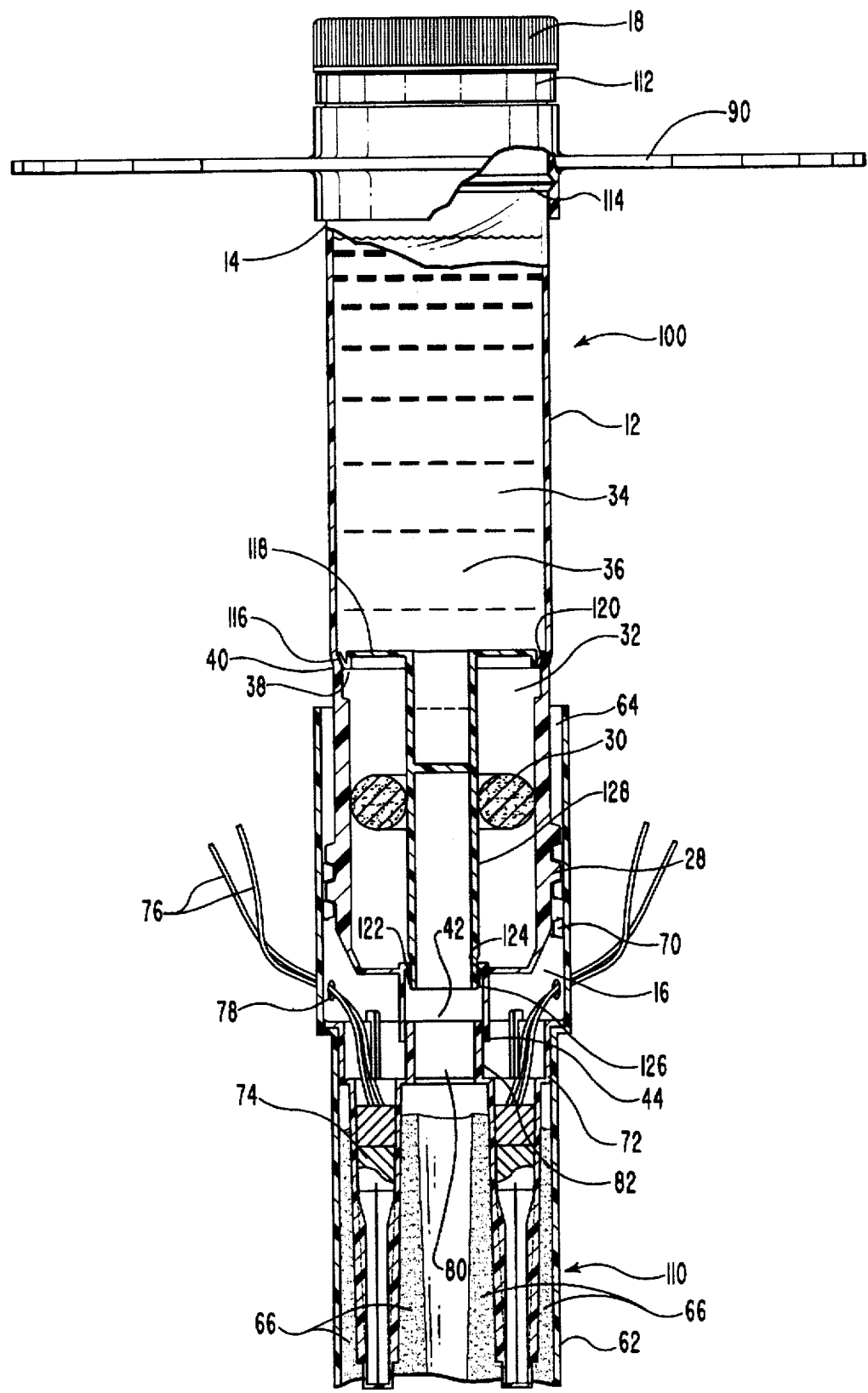
FIG. 7 is a partial cross-sectional elevation view like that of FIG. 4, but of a second embodiment of a bioremediation apparatus immediately incorporating teachings of the present invention immediately upon becoming fully coupled with an explosive apparatus.
Figure 8:
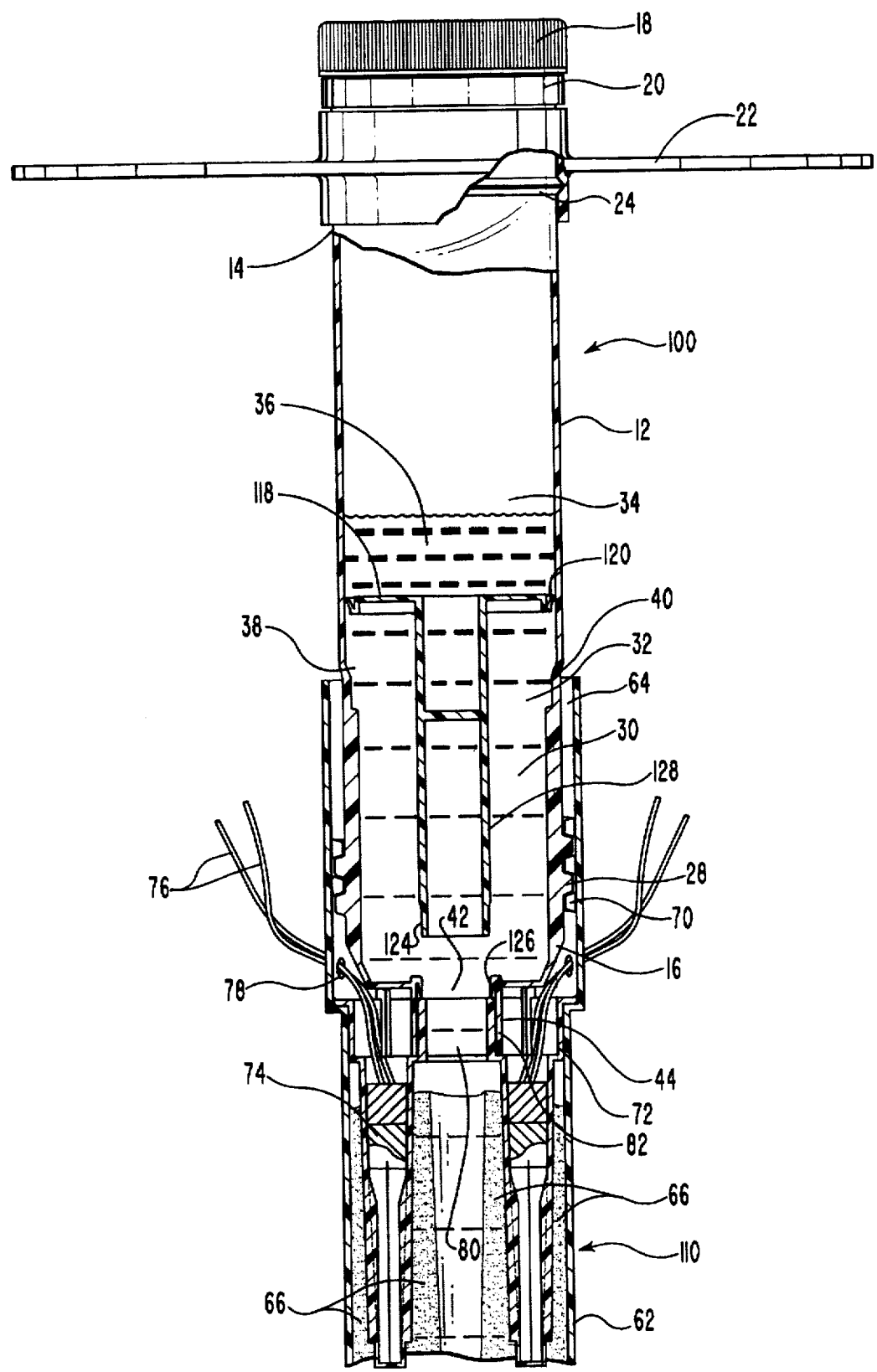
FIG. 8 is a partial cross-sectional elevation view like that of FIG. 6, but of the second embodiment of the bioremediation apparatus and the explosive apparatus illustrated in FIG. 7 at a time subsequent to that illustrated in FIG. 7 at which the explosive material in the explosive apparatus illustrated is contacted by hydrated microorganisms.

FIGS. 7 and 8 depict a second embodiment of a system for in situ bioremediating of an explosive according to teachings of the present invention. The system shown there comprises a bioremediation apparatus 100 and an explosive apparatus 110. Components shown in FIGS. 7 and 8 that are identical to the components shown in FIGS. 1–6 are identified with the same reference characters as are the corresponding components in FIGS. 1–6.

Bioremediation apparatus 100 has a cap 18, a spacer 112, and an anchor member 90 that encircles top end 14 of casing 12. Cap 18 and a spacer 112 are configured to maintain anchor member 90 on a nib 114. Cap 18 has cap threads 24 which cooperate with end threads 26 around top end 14 of casing 12 to seal top end 14 of casing 12. Spacer 112 is positioned between cap 18 and anchor member 90. Spacer 112 has a bottom portion not shown in the figures that is positioned within the top end of anchor member 90. When the system of FIGS. 7 and 8 is pushed down a borehole with a tamping pole, anchor member 90 cannot be dislodged from nib 114, since anchor member 90 abuts spacer 112, and cap 18 retains spacer 112 in position.

Solution 34 is contained in reservoir chamber 36 and is released to hydrate microorganism 30 in storage chamber 32 when a first valve 116 in solution passage 38 is opened. First valve 116 comprises the interior of neck 40 and a first valve member 118. First valve member 118 has a lip end 120 around the perimeter of first valve member 118. Lip end 120 is tapered to correspond to the dimensions of the interior of neck 40 and is flexible, thereby to form a fluid seal with solution passage 38.

A second valve 122 comprises a second valve member 124 and a lip seal member 126o Second valve member 124 is the tapered bottom end of a valve connector 128. Lip seal member 126 extends from sleeve member 44 into bioremediation outlet 42 to form a fluid seal with second valve member 124.

First valve member 118 is integrally formed with valve connector 128, and valve connector 128 is integral with second valve member 124. Accordingly, first valve member 118, valve connector 128, and second valve member 124 together form an integral divider. In the first embodiment shown in FIGS. 1–6, the first valve means is also connected to the second valve means, as first valve member 48 and second valve member 54 are connected by valve connector 56. Thus, both in the first embodiment of FIGS. 1–6 and in the second embodiment of FIGS. 1–8, at least a portion or a component of each valve means is connected to at least a portion or a component of the other valve means.

The coupling means for coupling a bioremediation apparatus with an explosive apparatus, such as the combination of casing threads 28 and shell threads 70 as shown in FIGS. 1–8, may further comprise a means for indicating the position of the valves. In the preferred embodiment, casing 12 has a bump not shown in the figures that causes a clicking noise when portal member 82 contacts the second valve member after casing threads 28 and shell threads 70 are advanced over each other. The clicking noise informs a user that the bioremediation apparatus and the explosive apparatus are coupled.

In yet additional alternative embodiments of apparatus incorporating the teachings of the present invention, a material such as gelatin, which is slowly self-effacing in the presence of microorganisms, is used to contain at least the microorganisms of the microorganism consortium. Thus, for example, it is within the scope of the present invention to perform the functions of either or both a first or second valve means according to the present invention using valve members comprised of a material, such as gelatin, which eventually degrades and releases the microorganisms. Alternatively, microorganisms encapsulated in gelatin may be releasably contained as in a storage means of the present invention for eventual contact with an explosive material. In another alternative embodiment, microorganisms encapsulated in gelatin are placed directly in contact with an explosive material.

Another method for reliably eliminating the hazards associated with undetonated explosives includes utilizing between explosive material 66 and microorganisms 30 a barrier designed to deteriorate within a reasonable, predetermined time. Careful structural and material design of such a barrier can produce relatively precisely timed releases. Microorganisms 30 are initially hydrated or are eventually hydrated when combined with a solution, such as solution 34. The barrier releases microorganisms 30, alone or in solution 34, to react with explosive material 66. Similar, effacing barriers can to advantage be interposed between solution 34 and microorganisms 30.

For example, microorganisms can be contained within a gelatin capsule which is placed on the explosive charge at the time of the installation of the explosive charge in a borehole. An example of a time release barrier which is a micro-scale bioremediation apparatus is a gelatin capsule containing microorganisms alone or in combination with moisture and nutrients that is pressed into the explosive charge at the time that the charge is manufactured as shown in FIG. 9.

Figure 9:
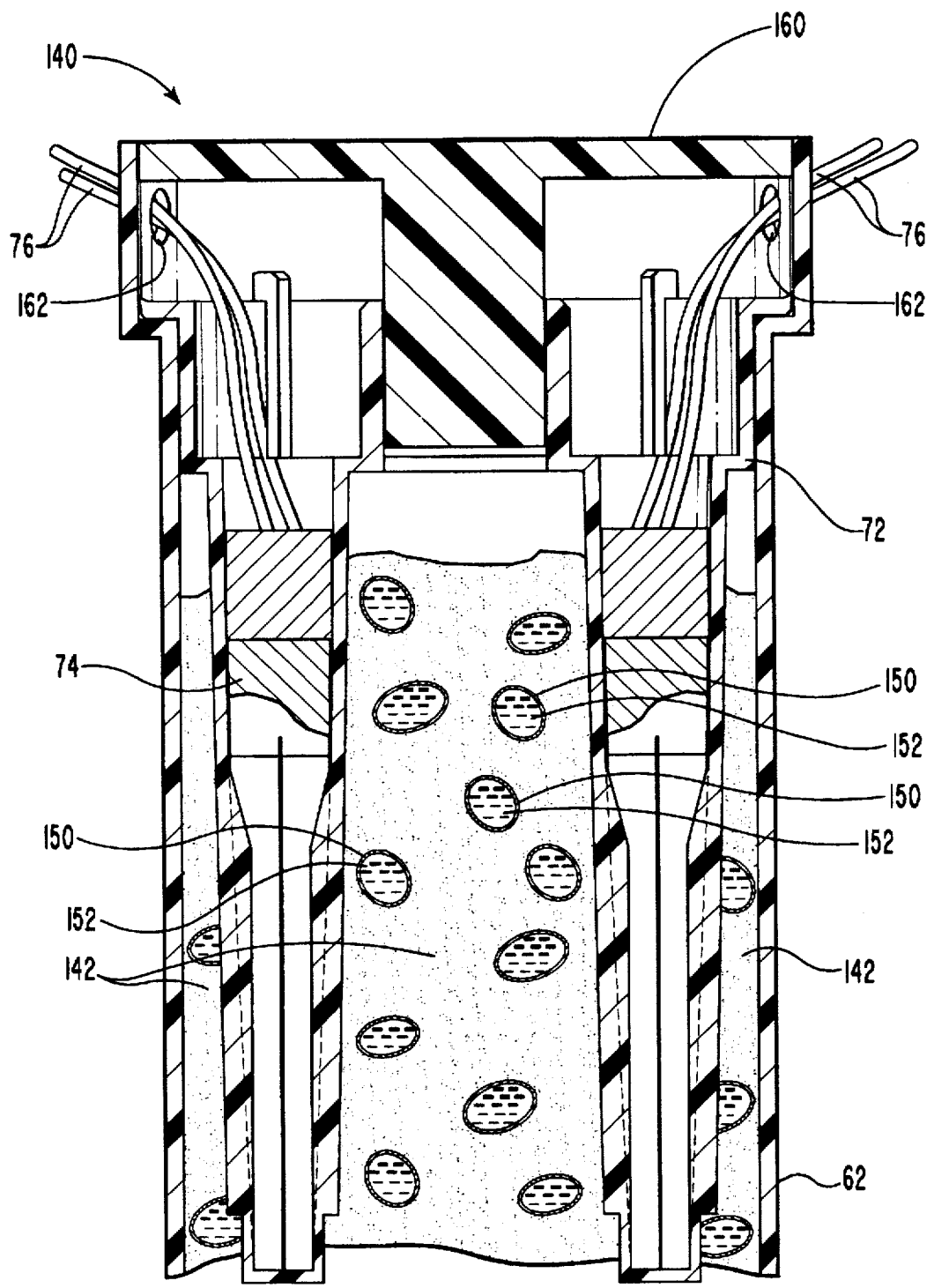
FIG. 9 is a cross-sectional elevation view of a third embodiment of an explosive apparatus that encloses an explosive material permeated by a plurality of micro-scale bioremediation apparatus according to the teachings of the present invention.

FIG. 9 illustrates an explosive apparatus 140 incorporating some of these teachings. Gelatin capsules 150 are shown containing a solution 152 of microorganisms, water, and nutrients, and dispersed throughout an explosive material 142 housed in a shell 62. Gelatin capsules 150 can be randomly dispersed, as shown, or concentrated as needed to initially and quickly deactivate the explosive charge. Explosive apparatus 140 is shown with an optional cap 160 and access openings 162 for wires 76.

Figure 10:
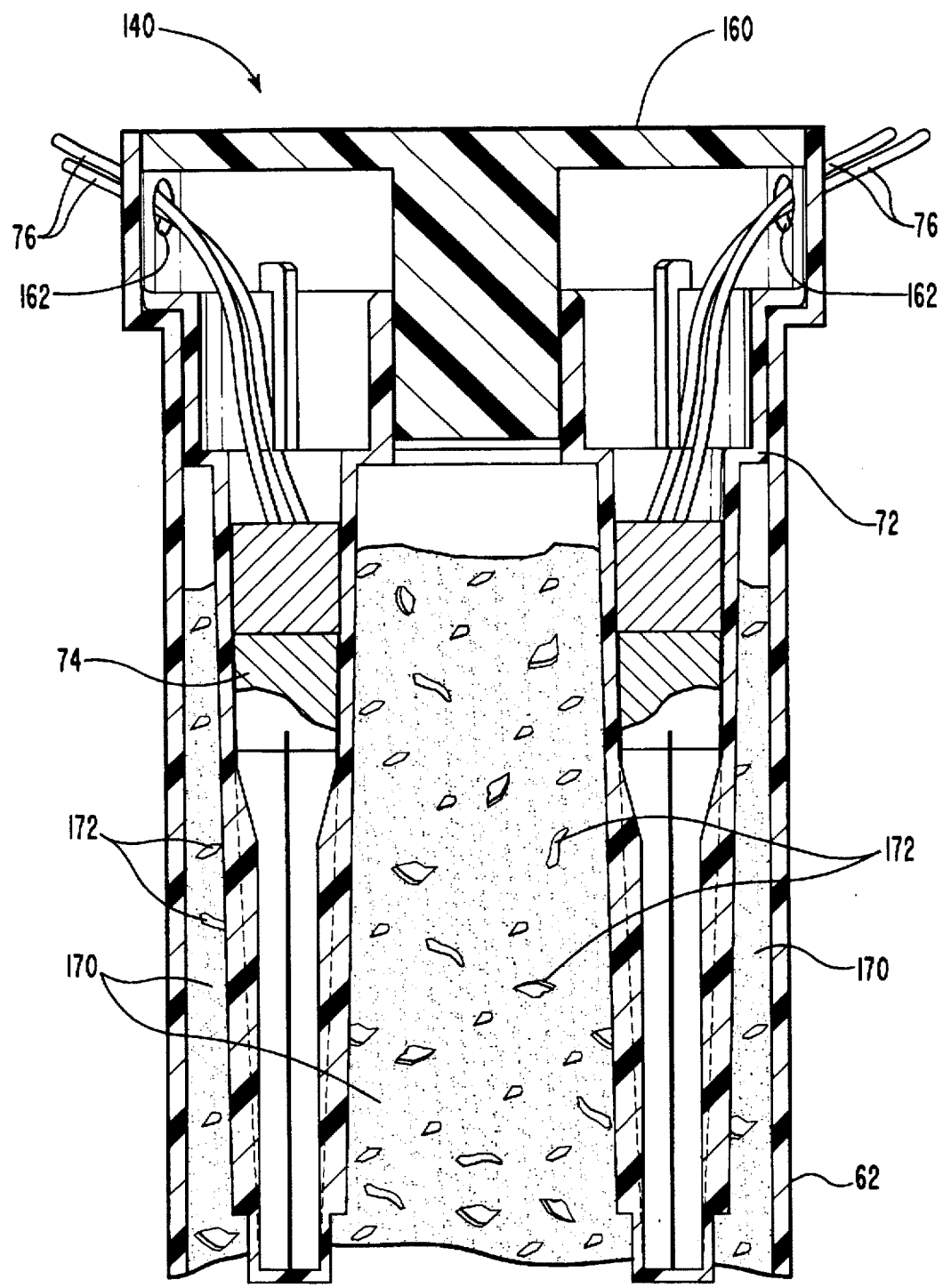
FIG. 10 is a cross-sectional elevation view of a fourth embodiment of an explosive apparatus housing an explosive material intermixed with microorganisms selected according to the teachings of the present invention as being microorganisms capable of biodegrading the explosive material.
Figure 3:
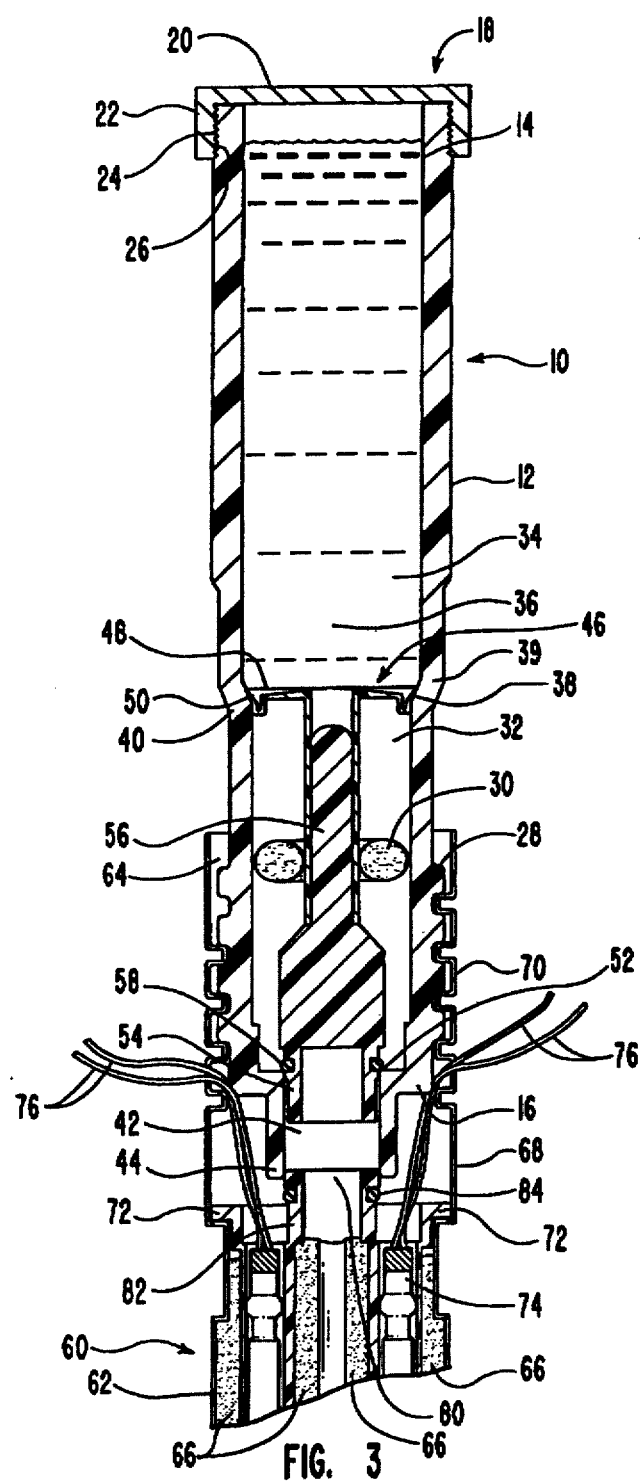
Figure 5:
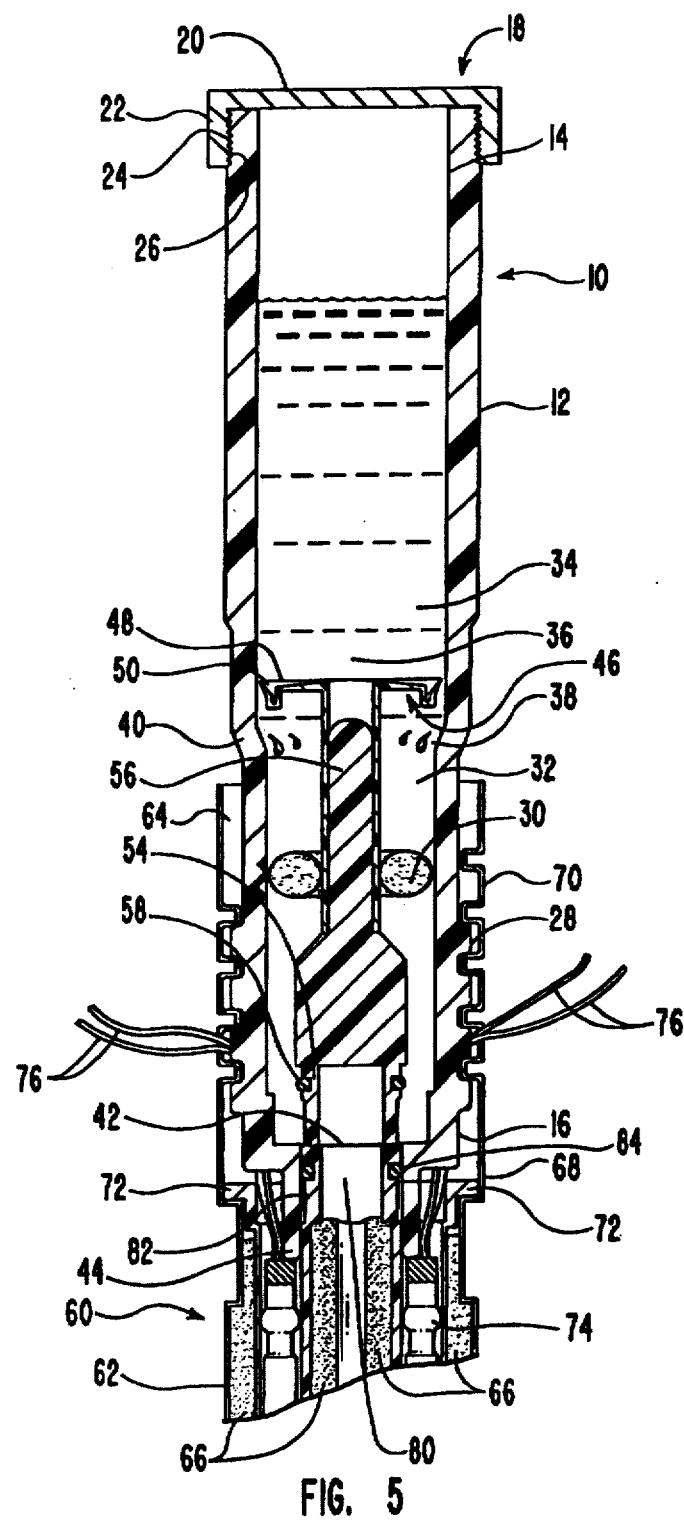
Figure 6:
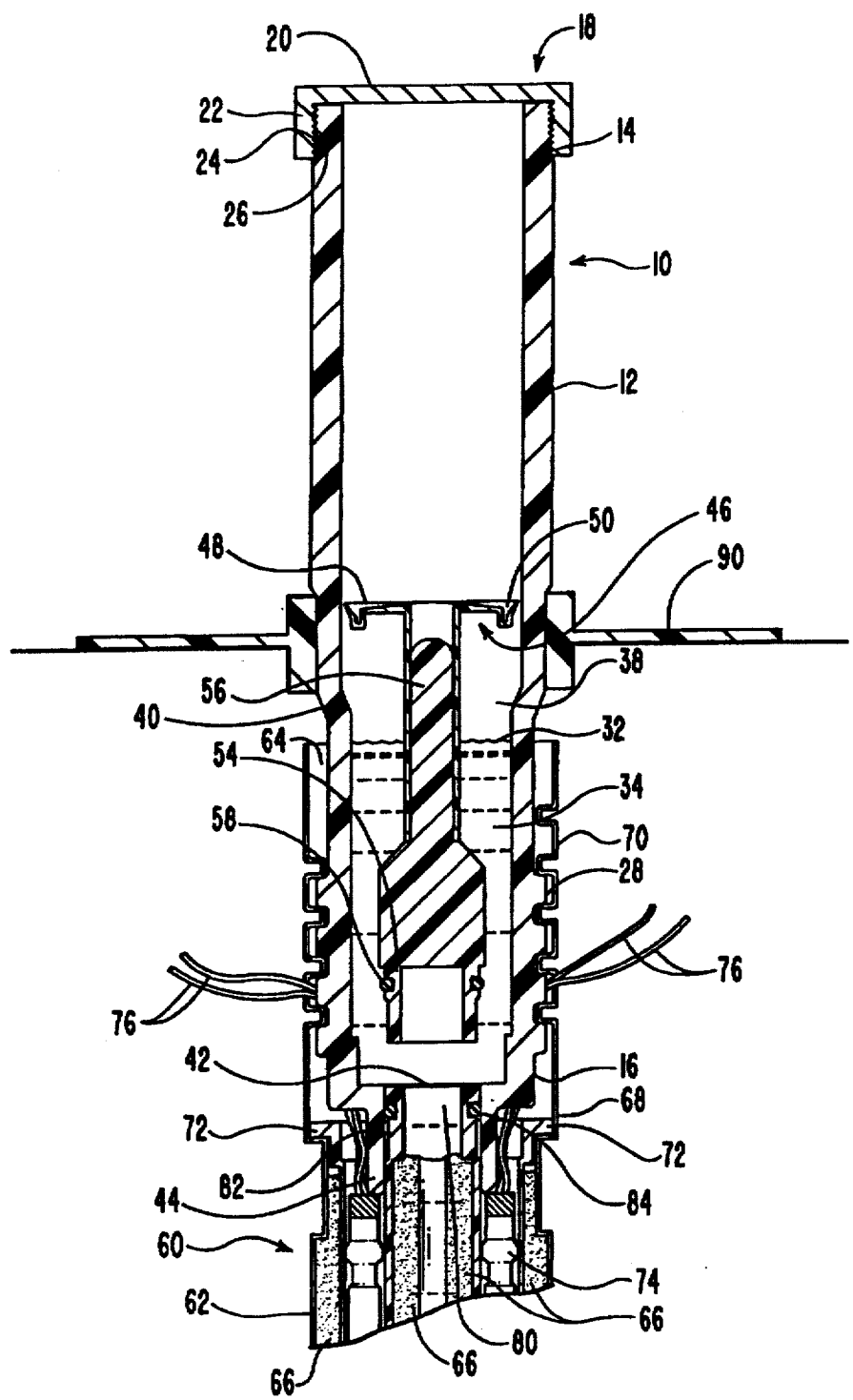

Another method for reliably remediating undetonated explosive material involves intermixing microorganisms with the explosive material to produce a mixture that is then shaped into an explosive charge that will bioremediate automatically within a predetermined time following manufacture. A corresponding apparatus is shown in FIG. 10. FIG. 10 depicts a second embodiment of an explosive apparatus 140 having a mixture of explosive material 170 and shards 172 of a moist nutrient wafer containing microorganisms.

The systems shown in FIG. 9 and FIG. 10, as well as comparable systems and methods, are not activated in the field and do not require the coupling of a distinct bioremediation apparatus with a corresponding explosive apparatus. Nonetheless, the systems so configured do have a shelf life, as each system will be disabled in due course, whether or not implanted or used at all.

The degradation rate is controlled by varying the amount and types of explosive material and the selection of microorganisms in the microorganism consortium.

Yet another method of bioremediating explosives involves installing an explosive charge in a detonation site, such as a borehole, and then positioning microorganisms around the explosive charge by depositing microorganisms directly on the explosive charge and the detonation site. Similarly, a solution of microorganisms can be deposited at a detonation site in solution form. Then the explosive charge is placed in the solution of microorganisms. Additionally, an explosive apparatus can be sprayed with or soaked in a solution of microorganisms before being installed at a given detonation site.

Experiments were conducted to study the process of remediating explosive materials according to the teachings of the present invention. To do so, a microorganism consortium was derived from soil and water samples obtained on the property of an established explosive manufacturer located at 8305 South Highway 6, Spanish Fork, Utah 84660 U.S.A. The microorganism consortium in the form of an aqueous solution was combined with various types of explosive materials, either in solid form or in an aqueous suspension, and the results were observed and documented. The results of several of these tests are set forth below as examples.

EXAMPLE 1

Quantities of the explosive materials TNT and PETN in water were combined with the aqueous solution of the microorganism consortium. The resulting mixture initially included 47.23 ppm of PETN and 40.63 parts per million (ppm) of TNT. The mixture was divided among containers that were stored in aerobic conditions at ambient temperature for various time periods. Table 1 below indicates the explosive analysis of these samples after each designated time interval. The explosive materials were substantially degraded after a period of five weeks.

TABLE 1

Aerobic Bioremediation of TNT and PETN

| Explosive Material | Initial Analysis | Analysis After 3 Days | Analysis After 5 Weeks |
|---|---|---|---|
| PETN | 47.23 ppm | 40.94 ppm | 7.25 ppm |
| TNT | 40.63 ppm | 5.32 ppm | 0.62 ppm |

EXAMPLE 2

The mixture prepared in Example 1 was stored in anaerobic conditions at ambient temperature and observed. The results were determined by HPLC analysis in ppm and averaged. Table 2 below sets forth the results obtained. As can be seen by comparing the results in Table 2 with the results in Table 1, the explosive materials tested remediated more rapidly under anaerobic conditions than under aerobic conditions.

TABLE 2

Anaerobic Bioremediation of PETN and TNT

| Explosive Material | Initial Analysis | Analysis after 3 Days | Analysis after 1 Week | Analysis after 5 Weeks |
|---|---|---|---|---|
| PETN | 47.23 ppm | 28.31 ppm | 24.46 ppm | 0.82 ppm |
| TNT | 40.63 ppm | 0.31 ppm avg. | 0.31 ppm avg. | None |

EXAMPLE 3

Discs of the explosive material Pentolite having a diameter of a pencil were split in two. When the discs were split each weighed about 0.1 gram. The discs were placed either in water as a control or in 6 ml to 8 ml of an aqueous solution of a microorganism consortium. After a specific amount of time in aerobic conditions, the discs were dried and weighed or analyzed by HPLC. The liquid portions were analyzed by HPLC. The net remediated weight loss in the explosive material was determined by subtracting the control weight loss as a percentage from the weight loss as a percentage in each remediated explosive. The explosive loss by degradation is listed in Table 3 for each of the samples.

TABLE 3

Aerobic Bioremediation of Pentolite

| Sample No. | Sample or Test | Time | Initial Weight | Final dry weight plus weight of explosive in liquid portion. | Net Remediated Weight Loss |
|---|---|---|---|---|---|
| A | Control | 22 days | 0.1355 g | 0.1266 g = 6.57% loss | 6.97% Net Loss |
| | Test | 22 days | 0.0981 g | 0.0848 g = 13.54% loss | |
| B | Control | 88 days | 0.0578 g | 0.0557 g = 3.63% loss | 5.52% Net Explosive Loss |
| | Test | 88 days | 0.0743 g | 0.0675 g = 9.15% | |
| C | Control | 173 days | 0.1236 g | 0.1236 g = no loss | 6.78% Net Explosive Loss |
| | Test | 173 days | 0.0737 g | 0.0687 g = 6.78% loss | |

EXAMPLE 4

Experiments were conducted to compare remediation rates under aerobic and anaerobic conditions. Separate 5 gram samples of PETN/TNT Pentolite in a ratio of 60:40 were analyzed and placed in 100 ml to 300 ml of an aqueous solution of a microorganism consortium. One was subjected to aerobic conditions; the other was subjected to anaerobic conditions. After various periods of time the samples were removed, air dried, and weighed to determine the amount of explosive material that had not degraded. The weight of the remaining explosive material was subtracted from original weight to determine the weight of the explosive material lost due to bioremediation. The results are listed in Table 4 below.

TABLE 4

Aerobic and Anaerobic Bioremediation of Pentolite

| Condition: Aerobic or Anaerobic | Original Weight | Time | Percent Wt Loss at Time listed | Time | Percent Wt Loss at Time Listed |
|---|---|---|---|---|---|
| Aerobic | 5.015 g | 66 days | 3.21% | 163 days | 5.43% |
| Anaerobic | 6.9027 g | — | — | 179 days | 3.10% |

EXAMPLE 5

Also investigated was the remediation according to the present invention of low levels of explosive materials in water. The explosive materials RDX and PETN were mixed with the water, combined with an aqueous solution of a microorganism consortium, and then stored. The samples were tested by HPLC for explosive content initially and after 2 weeks. As shown in Table 5 below the bioremediation was nearly complete after two weeks.

TABLE 5

Bioremediation of Aqueous Solution of RDX and PETN

| Explosive Material | Initial Analysis | Analysis after 2 weeks |
|---|---|---|
| RDX | 6.6 ppm | Not detected |
| PETN | 25.0 ppm | Less than 0.5 ppm |

EXAMPLE 6

The remediation according to the present invention of soil contaminated with an explosive material was also investigated. Soil contaminated with the explosive material PETN was mixed with an aqueous solution of a microorganism consortium and stored at ambient temperature. Samples were analyzed initially, after 44 days, and finally after 125 days. The PETN content in the soil dropped from 1659 ppm to 551 parts per million (ppm). The results are set forth in Table 6 below.

TABLE 6

Bioremediation of Soil Contaminated with PETN

| Initial Analysis | Analysis after 44 Days | Analysis after 125 Days |
|---|---|---|
| 1659.2 ppm | 1193.2 ppm | 551.8 ppm |

The present invention may be embodied in other specific forms without departing from its spirit or essential characteristics. The described embodiments are to be considered in all respects only as illustrated and not restrictive. The scope of the invention is, therefore; indicated by the appended claims rather than by the foregoing description. All changes which come within the meaning and range of equivalency of the claims are to be embraced within their scope.

What is claimed is:

1. A system for in situ remediating of an explosive, if the explosive fails to detonate, the system comprising:
   a. a bioremediation apparatus comprising:
      i. reservoir means for releasably containing a solution for mixing with microorganisms;
      ii. storage means for releasably containing at least one type of microorganism capable of bioremediating an explosive material, the storage means being positioned below the reservoir means and being in communication with the reservoir means;
      iii. first valve means for releasing the solution from the reservoir means into the storage means to hydrate the microorganisms in the storage means when the first valve means is opened, the first valve means being at least partially disposed within the reservoir means;
      iv. second valve means for releasing the microorganisms and the solution from the storage means when the second valve means is opened, the second valve means being connected to the first valve means and being at least partially disposed within the storage means; and
   b. an explosive apparatus configured for coupling to the bioremediation apparatus, said explosive apparatus comprising:
      i. a shell having an open end;
      ii. a quantity of an explosive material contained in the shell;
      iii. a capwell positioned in the open end of the shell and having a bioremediation portal formed therethrough communicating with the explosive material in the shell; and
      iv. actuation means on the capwell for opening the first valve means and the second valve means when the explosive apparatus is coupled to the bioremediation apparatus, thereby to release the microorganisms and the solution from the storage means for passage through the bioremediating portal to the explosive material.

2. A system as recited in claim 1, further comprising a valve connector for connecting a first valve member of the first valve means with a second valve member of the second valve means.

3. A system as recited in claim 1, wherein said reservoir means comprises a reservoir chamber, said reservoir chamber comprising:
   a. sidewalls defined by a casing;
   b. a top defined by cap means for sealing a top end of the casing; and
   c. a bottom defined by said first valve means.

4. A system as recited in claim 1, wherein said storage means comprises a storage chamber, said storage chamber comprising:
   a. sidewalls defined by a casing;
   b. a top defined by said first valve means; and
   c. a bottom defined by said second valve means.

5. A system as recited in claim 1, further comprising a casing of the bioremediation apparatus containing the reservoir means and the storage means and further comprising coupling means for coupling the bioremediation apparatus with the explosive apparatus, the coupling means being an extension of the casing and of the shell of the explosive apparatus.

6. A system as recited in claim 1, wherein the type of microorganism is selected from the group of microorganisms consisting of Pseudomonas spp., *Escherichia coli*, *Morganella morganii*, Rhodococcus spp., Comamonas spp., and denitrifying bacteria.

7. A system as recited in claim 6, wherein the type of microorganism is selected from the group of microorganisms in Pseudomonas spp. consisting of aeruginosa, fluorescens, acidovorans, mendocina, and cepacia.

8. A system as recited in claim 1, wherein the explosive material is selected from the group of explosive materials consisting of organic nitroaromatic explosives, organic nitramine explosives, and organic nitric ester explosives.

9. A system as recited in claim 1, wherein the explosive material is selected from the group of explosive materials consisting of trinitrotoluene, hexanitrostilbene, hexanitroazobenzene, diaminotrinitrobenzene, triaminotrinitrobenzene, cyclotrimethylene trinitramine, cyclotetramethylene tetranitramine, nitroguanidine, 2,4,6-trinitrophenylmethylnitramine, pentaerythritol tetranitrate, nitroglycerine, and ethylene glycol dinitrate.

10. A system as recited in claim 1, wherein the type of microorganism is one of a plurality of types of microorganisms that together with the type of microorganism define a microorganism consortium.

11. A system as recited in claim 10 wherein said microorganism consortium corresponds to the microorganism consortium identified at the American Type Culture Collection by ATCC Designation No. 55784.

12. A system for in situ remediating an explosive, if the explosive fails to detonate, the system comprising:
   a. a bioremediation apparatus comprising:
      i. a casing;
      ii. a reservoir chamber having sidewalls defined by the casing;

iii. a solution releasably contained within the reservoir chamber for mixing with microorganisms;

iv. a storage chamber having sidewalls defined by the casing, in communication with the reservoir chamber through a solution passage, and having a bioremediation outlet passing through the casing;

v. at least one species of microorganisms capable of bioremediating an explosive material being releasably contained within the storage chamber;

vi. first valve means for releasing the solution from the reservoir chamber through the solution passage to the storage chamber to hydrate the microorganisms in the storage chamber when the first valve means is opened, the first valve means being at lease partially disposed within the reservoir chamber; and vii. second valve means for releasing the microorganisms and the solution from the storage means when the second valve means is opened, the second valve means being connected to the first valve means and being at least partially disposed within the storage means; and b. an explosive apparatus configured for coupling to the bioremediation apparatus, said explosive apparatus comprising:

i. a shell having an open end;

ii. a quantity of an explosive material contained in the shell;

iii. a capwell positioned in the open end of the shell and having a bioremediation portal formed therethrough communicating with the explosive material in the shell; and iv. actuation means on the capwell for opening the first valve means and the second valve means when the explosive apparatus is coupled to the bioremediation apparatus, thereby to release the microorganisms and the solution from the storage chamber for passage through the bioremediating portal to the explosive material.

13. A system as recited in claim 12, further comprising a valve connector for connecting a first valve member of the first valve means with a second valve member of the second valve means.

14. A system as recited in claim 12, wherein the first valve means defines the bottom of the reservoir chamber and the top of the storage chamber, and wherein the second valve defines the bottom of the storage chamber.

15. A system as recited in claim 12, further comprising coupling means for coupling the bioremediation apparatus with the explosive apparatus, the coupling means being an extension of the casing and of the shell of the explosive apparatus.

16. A system as recited in claim 12, wherein the type of microorganism is selected from the group of microorganisms consisting of Pseudomonas spp., *Escherichia coli*, *Morganella morganii*, Rhodococcus spp., Comamonas spp., and denitrifying bacteria.

17. A system as recited in claim 16, wherein the type of microorganism is selected from the group of microorganisms in Pseudomonas spp. consisting of aeruginosa, fluorescens, acidovorans, mendocina, and cepacia.

18. A system as recited in claim 12, wherein the explosive material is selected from the group of explosive materials consisting of organic nitroaromatic explosives, organic nitramine explosives, and organic nitric ester explosives.

19. A system as recited in claim 12, wherein the explosive material is selected from the group of explosive materials consisting of trinitrotoluene, hexanitrostilbene, hexanitroazobenzene, diaminotrinitrobenzene, triaminotrinitrobenzene, cyclotrimethylene trinitramine, cyclotetramethylene tetranitramine, nitroguanidine, 2,4,6-trinitrophenylmethylnitramine, pentaerythritol tetranitrate, nitroglycerine, and ethylene glycol dinitrate.

20. A system as recited in claim 10, wherein the type of microorganism is one of a plurality of types of microorganisms that together with the type of microorganism define a microorganism consortium.

21. A system as recited in claim 20 wherein said microorganism consortium corresponds to the microorganism consortium identified at the American Type Culture Collection by ATCC Designation No. 55784.

22. A system for in situ remediating of an explosive, if the explosive fails to detonate, the system comprising:

a. a bioremediation apparatus comprising:

i. a casing having a top end and a bottom end;

ii. a reservoir chamber defined by the casing;

iii. a solution releasably contained within the reservoir chamber for mixing with microorganisms;

iv. a storage chamber defined by the casing, positioned below the reservoir chamber, in communication with the reservoir chamber through a solution passage, and having a bioremediation outlet through the bottom end of the casing;

v. at least one type of microorganism capable of bioremediating an explosive material releasably contained within the storage chamber;

vi. first valve means for delivering the solution from the reservoir chamber by gravity through the solution passage to the storage chamber to hydrate the microorganisms in the storage chamber when the first valve means is opened; and vii. second valve means for delivering the hydrated microorganisms and the solution from the storage chamber when the second valve means is opened, and b. an explosive apparatus configured for coupling to the bioremediation apparatus, said explosive apparatus comprising:

i. a shell having an open end;

ii. a quantity of an explosive material contained in the shell;

iii. a capwell positioned in the open end of the shell and having a bioremediation portal formed therethrough communicating with the explosive material in the shell; and iv. actuation means on the capwell for opening the first valve means and the second valve means when the explosive apparatus is coupled to the bioremediation apparatus, thereby to release the microorganisms and the solution from the storage chamber for passage through the bioremediating portal to the explosive material.

23. A system as recited in claim 22, further comprising cap means for sealing the top end of the casing.

24. A system as recited in claim 22, further comprising a valve connector for connecting a first valve member of the first valve means with a second valve member of the second valve means.

25. A system as recited in claim 22, wherein the first valve means defines the bottom of the reservoir chamber and the top of the storage chamber, and wherein the second valve defines the bottom of the storage chamber.

26. A system as recited in claim 22, further comprising coupling means for coupling the bioremediation apparatus with the explosive apparatus, the coupling means being an extension of the casing and of the shell of the explosive apparatus.

27. A system as recited in claim 22, wherein the type of microorganisms is selected from the group of microorganisms consisting of Pseudomonas spp., *Escherichia coli*, *Morganella morganii*, Rhodococcus spp., Comamonas spp., and denitrifying bacteria.

28. A system as recited in claim 27, wherein the type of microorganism is selected from the group of microorganisms in Pseudomonas spp. consisting of aeruginosa, fluorescens, acidovorans, mendocina, and cepacia.

29. A system as recited in claim 22, wherein the explosive material is selected from the group of explosive materials consisting of organic nitroaromatic explosives, organic nitramine explosives, and organic nitric ester explosives.

30. A system as recited in claim 22, wherein the explosive material is selected from the group of explosive materials consisting of trinitrotoluene, hexanitrostilbene, hexanitroazobenzene, diaminotrinitrobenzene, triaminotrinitrobenzene, cyclotrimethylene trinitramine, cyclotetramethylene tetranitramine, nitroguanidine, 2,4,6-trinitrophenylmethylnitramine, pentaerythritol tetranitrate, nitroglycerine, and ethylene glycol dinitrate.

31. A system as recited in claim 22, wherein the type of microorganism is one of a plurality of types of microorganisms that together with the type of microorganism define a microorganism consortium.

32. A system as recited in claim 31 wherein said microorganism consortium corresponds to the microorganism consortium identified at the American Type Culture Collection by ATCC Designation No. 55784.

33. A system for in situ remediating of an explosive, if the explosive fails to detonate, the system comprising:
   a. a bioremediation apparatus comprising:
      i. a casing having a top end and a bottom end;
      ii. a reservoir chamber defined by the casing;
      iii. a solution releasably contained within the reservoir chamber for mixing with microorganisms;
      iv. a storage chamber defined by the casing, positioned below the reservoir chamber, in communication with the reservoir chamber through a solution passage, and having a bioremediation outlet through the bottom end of the casing;
      v. at least one type of microorganism capable of bioremediating an explosive material releasably contained within the storage chamber;
      vi. first valve for delivering the solution from the reservoir chamber by gravity through the solution passage to the storage chamber to hydrate the microorganisms in the storage chamber when the first valve means is opened; and
      vii. second valve for delivering the microorganisms and the solution from the storage chamber by gravity through the bioremediation outlet of the casing and the bioremediation portal of the shell to contact the explosive when the second valve is opened, the second valve being connected to the first valve by a connector and being at least partially disposed within the storage chamber; and
   b. an explosive apparatus configured for coupling to the bioremediation apparatus, said explosive apparatus comprising:
      i. a shell having an open end;
      ii. a quantity of an explosive material contained in the shell;
      iii. a capwell positioned in the open end of the shell and having a bioremediation portal formed therethrough communicating with the explosive material in the shell; and
      iv. actuation means on the capwell for opening the first valve and the second valve when the explosive apparatus is coupled to the bioremediation apparatus, thereby to release the microorganisms and the solution from the storage chamber for passage through the bioremediating portal to the explosive material.

34. A system as recited in claim 23, further comprising cap means for sealing the top end of the casing.

35. A system as recited in claim 23, wherein the first valve defines the bottom of the reservoir chamber and the top of the storage chamber, and wherein the second valve defines the bottom of the storage chamber.

36. A system as recited in claim 33, further comprising coupling means for coupling the bioremediation apparatus with the explosive apparatus, the coupling means being an extension of the casing and of the shell of the explosive apparatus.

37. A system as recited in claim 33, wherein the type of microorganism is selected from the group of microorganisms consisting of Pseudomonas spp., *Escherichia coli*, *Morganella morganii*, Rhodococcus spp., Comamonas spp., and denitrifying bacteria.

38. A system as recited in claim 37, wherein the type of microorganism is selected from the group of microorganisms in Pseudomonas spp. consisting of aeruginosa, fluorescens, acidovorans, mendocina, and cepacia.

39. A system as recited in claim 33, wherein the explosive material is selected from the group of explosive materials consisting of organic nitroaromatic explosives, organic nitramine explosives, and organic nitric ester explosives.

40. A system as recited in claim 33, wherein the explosive material is selected from the group of explosive materials consisting of trinitrotoluene; hexanitrostilbene, hexanitroazobenzene, diaminotrinitrobenzene, triaminotrinitrobenzene, cyclotrimethylene trinitramine, cyclotetramethylene tetranitramine, nitroguanidine, 2,4,6-trinitrophenylmethylnitramine, pentaerythritol tetranitrate, nitroglycerine, and ethylene glycol dinitrate.

41. A system as recited in claim 33, wherein the type of microorganism is one of a plurality of types of microorganisms that together with the type of microorganism define a microorganism consortium.

42. A system as recited in claim 41 wherein said microorganism consortium corresponds to the microorganism consortium identified at the American Type Culture Collection by ATCC Designation No. 55784.

43. A system for in situ remediating of an explosive if the explosive fails to detonate, the system comprising:
   a. a bioremediation apparatus comprising:
      i. storage means for releasably containing at least one type of microorganism capable of bioremediating an explosive material;
      ii. divider means for releasing the microorganisms from the storage means when the divider means is opened; and
   b. an explosive apparatus configured for coupling to the bioremediation apparatus, said explosive apparatus comprising:
      i. a shell having an open end;
      ii. a quantity of an explosive material contained in the shell;
      iii. a capwell positioned in the open end of the shell and having a bioremediation portal formed therethrough communicating with the explosive material in the shell; and
      iv. actuation means on the capwell for opening the divider means when the explosive apparatus is coupled to the bioremediation apparatus, thereby to release the microorganisms from the storage means for passage through the bioremediating portal to the explosive material.

44. A system as recited in claim 43, wherein the microorganisms are in a solution.

45. A system as recited in claim 43, wherein the microorganisms are encapsulated in gelatin.

46. A system as recited in claim 43, wherein the divider means is formed from gelatin.

47. A system as recited in claim 44, further comprising coupling means for coupling the bioremediation apparatus with the explosive apparatus, the coupling means being an extension of a casing containing the storage means and the divider means, the coupling means also being an extension of the shell of the explosive apparatus.

48. A system as recited in claim 44, wherein the type of microorganisms is selected from the group of microorganisms consisting of Pseudomonas spp.; *Escherichia coli*, *Morganella morganii*, Rhodococcus spp., Comamonas spp., and denitrifying bacteria.

49. A system as recited in claim 48, wherein the type of microorganism is selected from the group of microorganisms in Pseudomonas spp. consisting of aeruginosa, fluorescens, acidovorans, mendocina, and cepacia.

50. A system as recited in claim 44, wherein the explosive material is selected from the group of explosive materials consisting of organic nitroaromatic explosives, organic nitramine explosives, and organic nitric ester explosives.

51. A system as recited in claim 44, wherein the explosive material is selected from the group of explosive materials consisting of trinitrotoluene, hexanitrostilbene, hexanitroazobenzene, diaminotrinitrobenzene, triaminotrinitrobenzene, cyclotrimethylene trinitramine, cyclotetramethylene tetranitramine, nitroguanidine, 2,4,6-trinitrophenylmethylnitramine, pentaerythritol tetranitrate, nitroglycerine, and ethylene glycol dinitrate.

52. A system as recited in claim 44, wherein the type of microorganism is one of a plurality of types of microorganisms that together with the type of microorganism define a microorganism consortium.

53. A system as recited in claim 52 wherein said microorganism consortium corresponds to the microorganism consortium identified at the American Type Culture Collection by ATCC Designation No. 55784.

54. A system for in situ remediating of an explosive, if the explosive fails to detonate, the system comprising:
 a. storage means for releasably containing at least one type of microorganism capable of bioremediating an explosive material; and
 b. a quantity of explosive material in contact with the storage means.

55. A system as recited in claim 54, wherein the storage means is formed from gelatin.

56. A system as recited in claim 54, wherein the type of microorganism is selected from the group of microorganisms consisting of Pseudomonas spp., *Escherichia coli*, *Morganella morganii*, Rhodococcus spp., Comamonas spp., and denitrifying bacteria.

57. A system as recited in claim 56, wherein the type of microorganism is selected from the group of microorganisms in Pseudomonas spp. consisting of aeruginosa, fluorescens, acidovorans, mendocina, and cepacia.

58. A system as recited in claim 54, wherein the explosive material is selected from the group of explosive materials consisting of organic nitroaromatic explosives, organic nitramine explosives, and organic nitric ester explosives.

59. A system as recited in claim 54, wherein the explosive material is selected from the group of explosive materials consisting of trinitrotoluene, hexanitrostilbene, hexanitroazobenzene, diaminotrinitrobenzene, triaminotrinitrobenzene, cyclotrimethylene trinitramine, cyclotetramethylene tetranitramine, nitroguanidine, 2,4,6-trinitrophenylmethylnitramine, pentaerythritol tetranitrate, nitroglycerine, and ethylene glycol dinitrate.

60. A system as recited in claim 54, wherein the type of microorganism is one of a plurality of types of microorganisms that together with the type of microorganism define a microorganism consortium.

61. A system as recited in claim 60 wherein said microorganism consortium corresponds to the microorganism consortium identified at the American Type Culture Collection by ATCC Designation No. 55784.

62. A system as recited in claim 1, wherein said first valve means is comprised of gelatin.

63. A system as recited in claim 1, wherein said second valve means is comprised of gelatin.

64. A system as recited in claim 12, wherein said first valve means is comprised of gelatin.

65. A system as recited in claim 12, wherein said second valve means is comprised of gelatin.

66. A system as recited in claim 22, wherein said first valve means is comprised of gelatin.

67. A system as recited in claim 22, wherein said second valve means is comprised of gelatin.

68. A system as recited in claim 33, wherein said first valve means is comprised of gelatin.

69. A system as recited in claim 33, wherein said second valve means is comprised of gelatin.

\* \* \* \* \*

UNITED STATES PATENT AND TRADEMARK OFFICE
CERTIFICATE OF CORRECTION

PATENT NO.   : 5,736,669
DATED        : April 7, 1998
INVENTOR(S)  : Ronald D. Thomas et al.

It is certified that error appears in the above-identified patent and that said Letters Patent is hereby corrected as shown below:

Title page,
The title page showing the illustrative figure should be replaced with the attached title page.

Drawings,
In the drawings, sheets 3, 5 and 6, consisting of Figures 3, 5 and 6, should be deleted to be replaced with sheets 3, 5 and 6, as shown on the attached pages.

Signed and Sealed this

Nineteenth Day of February, 2002

Attest:

JAMES E. ROGAN
*Attesting Officer*      *Director of the United States Patent and Trademark Office*

United States Patent [19]
Thomas et al.

[11] Patent Number: 5,736,669
[45] Date of Patent: Apr. 7, 1998

[54] SYSTEMS FOR BIOREMEDIATING EXPLOSIVES

[75] Inventors: Ronald D. Thomas, Woodland Hills; Lyman G. Bahr, Payson, both of Utah; Walter B. Dunning, Sonora, Calif.; Dean F. Richards, Pleasant Grove, Utah

[73] Assignee: The Ensign-Bickford Company, Simsbury, Conn.

[21] Appl. No.: 658,142

[22] Filed: Jun. 4, 1996

Related U.S. Application Data

[63] Continuation-in-part of Ser. No. 560,074, Nov. 17, 1995, abandoned.

[51] Int. Cl.$^6$ .................................... F42C 3/02
[52] U.S. Cl. ................ 102/293; 588/203; 435/262.5
[58] Field of Search .................... 102/293, 473; 588/202, 203; 86/49, 50; 89/1.11; 435/262.5

[56] References Cited

U.S. PATENT DOCUMENTS

| | | | |
|---|---|---|---|
| 2,330,110 | 9/1943 | Buchan | 166/21 |
| 3,157,119 | 11/1964 | Porter | 102/21.8 |
| 3,710,718 | 1/1973 | Grant | 102/23 |
| 4,016,117 | 4/1977 | Griffin | 260/17.4 |
| 4,064,941 | 12/1977 | Smith | 166/300 |
| 4,108,728 | 8/1978 | Spinner et al. | 195/127 |

(List continued on next page.)

OTHER PUBLICATIONS

Kaplan, David A., "Biotechnology and Bioremediation for Organic Energetic Compounds," *Organic Energetic Compounds* 373–416 (Paul L. Marinkas ed., 1996).

R. Boopathy et al., *Biological Transformation of 2,4,6-Trinitrotoluene (TNT) By Soil Bacteria Isolated From TNT-Contaminated Soil*, 47 Bioresource Technology 19 (1994).

R. Boopathy et al., *Biotransformation of 2,4,6-Trinitrotoluene (TNT) By Co-Metabolism With Various Co-Substrates: A Laboratory-Scale Study*, 47 Bioresource Technology 205 (1994).

John P. Knezovich et al., *Chemical and Biological Systems for Treating Waste Streams Contaminated with High Explosives*, paper submitted for JANNAF Safety and Environmental Protection Subcommittee Meeting in Tampa, Florida (Dec. 5–8, 1995).

John P. Knezovich et al., *Chemical and Biological Systems for Regenerating Activated Carbon Contaminated with High Explosives*, paper submitted to Proceedings Demin'94 in Luxembourg, Luxembourg (Nov. 14–16, 1994).

Primary Examiner—Charles T. Jordan
Assistant Examiner—John R. Hardee
Attorney, Agent, or Firm—Trask, Britt & Rossa

[57] ABSTRACT

Technology for in situ remediation of undetonated explosive material. A bioremediating apparatus in the form of a storage chamber houses in moist condition type of microorganisms capable of metabolizing the explosive material. Examples of such microorganisms include Pseudomonas spp., *Escherichia coli*, *Morganella morganii*, Rhodococcus spp., Comamonas spp., and denitrifying bacteria. The bioremediating apparatus is joined with an explosive apparatus that houses a charge of explosive material. A solution released into the storage chamber by opening a first valve hydrates the microorganisms. The explosive assembly has an actuation means for opening the first valve and a second valve that releases the microorganisms from the storage chamber to begin metabolizing the explosive material, when the explosive apparatus is joined with the bioremediating apparatus. If the explosive material fails to detonate, the explosive is remediated by the action of the microorganisms. Remediation includes both disabling of the explosive material and detoxification of the resulting chemical compositions. The valves utilized are either mechanical, and thus opened by the coupling of the bioremediating apparatus to the explosive apparatus, or comprised of a slowly effacing material, such as gelatin. A micro-scale form of a bioremediating apparatus includes microorganisms encapsulated in gelatin for disposition mixed in or contacting the explosive material.

69 Claims, 10 Drawing Sheets

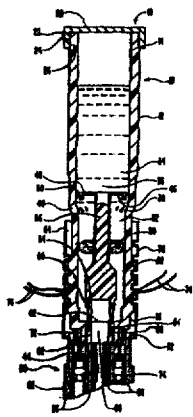

UNITED STATES PATENT AND TRADEMARK OFFICE
CERTIFICATE OF CORRECTION

PATENT NO. : 5,736,669
DATED : April 7, 1998
INVENTOR(S) : Ronald D. Thomas et al.

It is certified that error appears in the above-identified patent and that said Letters Patent is hereby corrected as shown below:

Title page,
First page, right column, line 8, change "Subcommitte" to -- Subcommittee --.

Column 2,
Lines 35 and 46, change the semicolon (";") to a comma (-- , --);

Column 3,
Line 4, change "sine" to -- site --; and
Line 47, change the semicolon (";") to a comma (-- , --).

Column 6,
Lines 3 and 18, change the semicolon (";") to a comma (-- , --).

Column 8,
Line 7, change "than" to -- that --.

Column 11,
Line 46, change "than" to -- that --.

Column 12,
Line 61, change the colon (":") to a comma (-- , --).

Column 13,
Line 36, after "126" change "o" to a period (-- . --).

Column 17,
Line 18, change "ppm" to -- parts per million (ppm) --; and
Line 34, change the semicolon (";") to a comma (-- , --).

Column 18, claim 1,
Line 6, change "bioremediating" to -- bioremediation --.

Column 19, claim 12,
Line 14, change "lease" to -- least --;
Lines 17 and 21, change "means" to -- chamber --; and
Line 37, change "bioremediating" to -- bioremediation --.

UNITED STATES PATENT AND TRADEMARK OFFICE
CERTIFICATE OF CORRECTION

PATENT NO. : 5,736,669
DATED : April 7, 1998
INVENTOR(S) : Ronald D. Thomas et al.

It is certified that error appears in the above-identified patent and that said Letters Patent is hereby corrected as shown below:

Column 19, claim 14,
Line 45, after "valve" insert -- means --.

Column 20, claim 20,
Line 6, change "10" to -- 12 --.

Column 20, claim 22,
Line 52, change "remediating" to -- remediation --.

Column 21, claim 33,
Line 44, change "the-storage" to -- the storage --;
Line 49, delete "means";
Line 53, change "the" to -- a -- (first and second occurrences); and Column 22,
Line 6, change "bioremediating" to -- bioremediation --.

Column 22, claim 34,
Line 7, change "23" to -- 33 --.

Column 22, claim 35,
Line 9, change "23" to -- 33 --.

Column 23, claim 43,
Line 3, change "bioremediating" to -- bioremediation --.

Column 24, claim 28,
Line 47, delete "means".

Column 24, claim 69,
Line 49, delete "means".

UNITED STATES PATENT AND TRADEMARK OFFICE
CERTIFICATE OF CORRECTION

PATENT NO. : 5,736,669
DATED : April 7, 1998
INVENTOR(S) : Ronald D. Thomas et al.

It is certified that error appears in the above-identified patent and that said Letters Patent is hereby corrected as shown below:

<u>Title page,</u>
At the end thereof add the following:

-- 5,370,845   12/1994   Miller et al.     422/186.3
   5,387,271   02/1995   Crawford et al.   71/9 --; and -- 5,578,488   11/1996   Tyndall et al.    435/262.5
   5,616,162   04/1997   Crawford et al.   71/9 --.

Signed and Sealed this

Fourteenth Day of May, 2002

Attest:

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO. : 5,736,669
DATED : April 7, 1998
INVENTOR(S) : Ronald D. Thomas et al.

It is certified that error appears in the above-identified patent and that said Letters Patent is hereby corrected as shown below:

Title page,
Item [56] References Cited after the reference 5,139,365 at the end thereof add the following:
-- 5,370,845   12/1994   Miller et al.   422/186.3
   5,387,271   02/1995   Crawford et al.   71/9 --; and Item [56] References Cited after the reference 5,610,062 at the end thereof add the following:
-- 5,578,488   11/1996   Tyndall et al.   435/262.5
   5,616,162   04/1997   Crawford et al.   71/9 --.

Signed and Sealed this

Twenty-first Day of May, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.   : 5,736,669
DATED        : April 7, 1998
INVENTOR(S)  : Ronald D. Thomas et al.

It is certified that error appears in the above-identified patent and that said Letters Patent is hereby corrected as shown below:

<u>Title page,</u>
Item [56], References Cited, page 2, left column, after the 5,139,365 reference add the following:
-- 5,370,845    12/1994    Miller et al.      422/186.3
   5,387,271    02/1995    Crawford et al.    71/9 --; and
after the 5,610,062 reference add the following:
-- 5,578,488    11/1996    Tyndall et al.     435/262.5
   5,616,162    04/1997    Crawford et al.    71/9 --.

Signed and Sealed this

Twenty-fifth Day of June, 2002

*Attest:*

*Attesting Officer*

JAMES E. ROGAN
*Director of the United States Patent and Trademark Office*